United States Patent [19]
Banks

[11] Patent Number: 6,069,157
[45] Date of Patent: May 30, 2000

[54] PARASITICIDAL COMPOUNDS

[75] Inventor: B. J. Banks, New York, N.Y.

[73] Assignee: Pfizer Inc., New York, N.Y.

[21] Appl. No.: 09/217,863

[22] Filed: Dec. 21, 1998

Related U.S. Application Data

[63] Continuation of application No. 08/978,247, Nov. 25, 1997, abandoned.

[51] Int. Cl.$^7$ .................. A61K 31/44; A61K 31/415; C07D 231/38; C07D 401/04
[52] U.S. Cl. .................. 514/341; 514/404; 546/275.4; 548/202; 548/247; 548/364.4; 548/365.7; 548/371.7; 548/375.1
[58] Field of Search .................. 546/275.4; 548/247, 548/365.7, 371.7, 375.1; 514/341

[56] References Cited

U.S. PATENT DOCUMENTS

| | | |
|---|---|---|
| 4,101,540 | 7/1978 | Coispeau . |
| 4,113,731 | 9/1978 | Winters et al. . |
| 4,122,278 | 10/1978 | Coispeau . |
| 5,104,439 | 4/1992 | Schallner et al. .................. 548/371.7 |
| 5,201,938 | 4/1993 | Costales et al. .................. 548/371.7 |

FOREIGN PATENT DOCUMENTS

| | | |
|---|---|---|
| 0641782 | 7/1992 | European Pat. Off. . |
| 2643640 | 4/1977 | Germany . |
| 1514862 | 9/1976 | United Kingdom . |
| 9213451 | 8/1992 | WIPO . |
| 9302055 | 2/1993 | WIPO . |
| 9319054 | 9/1993 | WIPO . |
| 9603516 | 2/1996 | WIPO . |

OTHER PUBLICATIONS

XP–002058484; Giovanni Meazza and Giampaolo Zanardi; A Convenient and Versatile Synthesis of 4–Trifluoromethyl–substituted Pyrazoles; J. Heterocyclic Chem., 30, 365 (1993).

XP–00205485; Carl J. Goddard; Antiinflammatory 1–Phenylpyrazole–4–Heteroarylakanoic Acids; J. Heterocyclic Chem., 28, 1607 (1991).

XP–002058486; Peter A. S. Smith, et al.; Isolation of Primary Decomposition Products of Azides; J. Org. Chem. vol. 35, No. 7, pp. 2215–2221, (1970).

XP–002058487; Pauline Cohen–Fernandes, et al.; Effects of Solvents and Steric Effects on UV and PMR spectra of 4–Phenylpyrazoles; Recueil, vol. 86, pp. 1249–1254, (1967).

XP–002058488; Par Jose Elguero, et al.; Etude UV de Pyrazoles; Bulletin De La Societe Chimique De France; No. 12, pp. 3744–3752, (1966).

XP–002058489; Rangnekar, D.W., et al.; Synthesis of Pendant 3–[1,2,3–triazol–2–yl]thieno[2,3–h]pyridines and their application on Polyester Fibers as Fluorescent Brighteners; Chemical Abstracts, vol. 117, No. 22, (1992).

XP–002058490; Vicentini, C.B.; Synthesis and Antifungal Activity of 4–thiazol–2–yl–5–aminopyrazoles and 4–aminopyrazolo–[3,4–c]isothiazoles; Chemical Abstracts, vol. 106, No. 21, (1987).

XP–002058491; Reddy, G. Jagath, et al.; Synthesis and Antifeedant activity of 3–(1–phenyl–1H–pyrazol–4–yl)benzofuran–2–carboxylic acids; Chemical Abstracts; vol. 101, No. 23, (1984).

XP–002058492; Identification Data—IDE.

XP–002058493; Identification Data—IDE.

EP 0 412 849 A2; Azole Pesticides; Robert John Willis, et al.; Aug. 10, 1990.

EP 0 412 849 A3; Azole Pesticides; Robert John Willis, et al.; Aug. 10, 1990.

EP 0 412 849 B1; Azole Pesticides; Robert John Willis, et al.; Aug. 10, 1990.

*Primary Examiner*—Robert W. Ramsuer
*Attorney, Agent, or Firm*—Peter C. Richardson; Paul H. Ginsburg; Lorraine B. Ling

[57] ABSTRACT

A new group of parasiticidal pyrazole derivatives has now been found. Thus, according to the present invention, there is provided a compound of formula (I),

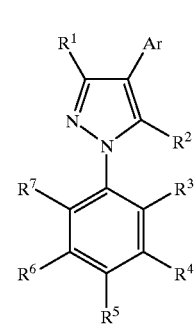

15 Claims, No Drawings

PARASITICIDAL COMPOUNDS

This application is a continuation of U.S. Ser. No. 08/978,247 filed Nov. 25, 1997, now abandoned.

This invention relates to pyrazole derivatives having parasiticidal properties.

Certain parasiticidal pyrazole derivatives are already known. These include fipronil (5-amino-3-cyano-1-(2,6-dichloro-4-trifluoromethylphenyl)-4-trifluoromethylsulphinylpyrazole) and certain analogues thereof mentioned in International Patent Application WO 87/03781.

International Patent Application WO 92/13451 and EP 0 412 849 A2 describe, inter alia, 4-(imidazol-2-yl)pyrazoles with pesticidal activity.

U.S. Pat. No. 4,614,534 and EP 0 205 023 A2 describe various 1-phenylpyrazoles substituted by a non-fused aromatic heterocycle at the 4-position and H or alkyl at the 3-position, such compounds being useful as herbicides and/or plant growth regulators.

U.S. Pat. No. 4,740,231 describes various 1-aryl-5-alkoximinoalkylaminopyrazoles as herbicides and plant growth regulators. Brief mention is also made of the insecticidal activity of these compounds in this publication.

EP 0 418 845 A1 discloses various 1-phenylpyrazoles with heterocyclic and aryl substituents on the pyrazole, such compounds being useful as medicaments with antiinflammatory, analgesic and immune system activity. No 4-aryl- or 4-heteroaryl-substituted pyrazoles are specifically disclosed by this publication.

A new group of parasiticidal pyrazole derivatives has now been found. Thus, according to the present invention, there is provided a compound of formula (I),

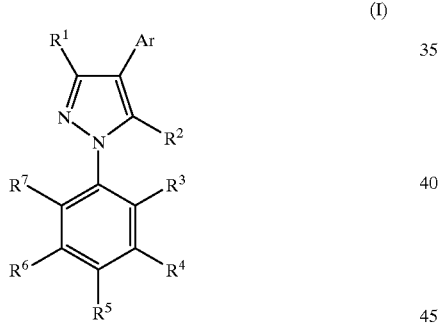

(I)

wherein $R^1$ is H, $C_{1-6}$ alkyl optionally substituted by one or more halogen atoms, halogen, CN, $C_{1-6}$ alkoxycarbonyl optionally substituted by one or more halogen atoms, $NO_2$, CHO, $CONH_2$, $CSNH_2$ or $C_{1-6}$ alkanoyl optionally substituted by one or more halogen atoms;

Ar is a ring "A" where "A" is a phenyl group, or "A" is a 5- or 6membered heteroaryl group, wherein heteroaryl means a fully unsaturated heterocycle, containing 1,2 or 3 hetero-atoms, which heteroatoms are independently selected from 1 N atom, 1 or 2 O atoms and 1 or 2 S atoms, where the valence allows, or Ar is a fused bicyclic moiety "AB" where the "A" ring is as defined above and the "B" ring fused thereto in "AB" is a 5- or 6-membered saturated or partially or fully unsaturated carbocycle, or saturated or partially or fully unsaturated heterocycle where the valence allows, which heterocycle contains 1,2,3 or 4 hetero-atoms independently selected from 1, 2, 3 or 4 N atoms, 1 or 2 O atoms and 1 or 2 S atoms, where the valence allows, said Ar group being linked via the "A" ring to the 4-position of the pyrazole via a carbon-carbon bond, and said Ar group being optionally substituted by one or more substituents independently selected from halogen, $C_{1-6}$ alkyl optionally substituted by one or more halogen atoms, $C_{1-6}$ alkoxy optionally substituted by one or more halogen atoms, $C_{1-6}$ alkoxycarbonyl optionally substituted by one or more halogen atoms, $NO_2$, $NH_2$, CN or $S(O)_m(C_{1-6}$ alkyl optionally substituted by one or more halogen atoms);

$R^2$ is H, halogen, $C_{1-6}$ alkyl optionally substituted by one or more halogen atoms, $C_{2-6}$ alkenyl optionally substituted by one or more halogen atoms, $C_{2-6}$ alkynyl optionally substituted by one or more halogen atoms, $N_2$, $NH(C_{1-6}$ alkanoyl optionally substituted by one or more halogen atoms), $NH(C_{1-6}$ alkoxycarbonyl optionally substituted by one or more halogen atoms), $N(C_{1-6}$ alkoxycarbonyl optionally substituted by one or more halogen atoms)$_2$, $NH(C_{1-6}$ alkyl optionally substituted by one or more halogen atoms), $N(C_{1-6}$ alkyl optionally substituted by one or more halogen atoms)$_2$, NHCONH ($C_{1-6}$ alkyl optionally substituted by one or more halogen atoms), N-pyrrolyl, NHCONH(phenyl optionally substituted by one or more halogen atoms), N=CH (phenyl optionally substituted by one or more halogen atoms), OH, $C_{1-6}$ alkoxy optionally substituted by one or more halogen atoms, SH or $S(O)_m(C_{1-6}$ alkyl optionally substituted by one or more halogen atoms);

$R^3$, $R^4$, $R^5$, $R^6$ and $R^7$ are each independently H, halogen, nitro, $C_{1-6}$ alkoxycarbonyl optionally substituted by one or more halogen atoms, $C_{1-6}$ alkyl optionally substituted by one or more halogen atoms, CN, $C_{1-6}$ alkanoyl optionally substituted by one or more halogen atoms, $CONH_2$, $CSNH_2$, $C_{1-6}$ alkoxy optionally substituted by one or more halogen atoms, $S(O)_m(C_{1-6}$ alkyl optionally substituted by one or more halogen atoms) or $SF_5$;

m is 0,1 or 2;

with the proviso that when $R^1$ is H or $C_{1-6}$ alkyl, $R^2$ is H, halogen, $NH_2$, $NH(C_{1-6}$ alkanoyl optionally substituted by one or more halogen atoms), $NH(C_{1-6}$ alk-oxycarbonyl optionally substituted by one or more halogen atoms), $N(C_{1-6}$ alkoxycarbonyl optionally substituted by one or more halogen atoms)$_2$, $NH(C_{1-6}$ alkyl optionally substituted by one or more halogen atoms), $NHCONH(C_{1-6}$ alkyl optionally substituted by one or more halogen atoms), NHCONH(phenyl optionally substituted by one or more halogen atoms), and $R^{3, R4}$, $R^5$, $R^6$ and $R^7$ are as defined for a compound of formula (I) then Ar is not a heteroaryl group "A";

or a pharmaceutically- or veterinarily-acceptable salt thereof (hereinafter referred to together as "the compounds of the invention").

The compounds of the invention are generally more efficacious or have a reduced resistance factor or have a broader spectrum of activity or are safer (e.g. less toxic) or have other more advantageous properties than the compounds of the prior art.

Alkyl, alkenyl and alkynyl groups may be straight, cyclic or branched where the number of carbon atoms allows. Alkanoyl, $S(O)_m$alkoxy, alkoxy and alkoxycarbonyl groups incorporate such alkyl moieties. Halogen means fluoro, chloro, bromo or iodo.

Pharmaceutically- or veterinarily-acceptable salts are well-known in the art and include, for example those mentioned by Berge et al in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, gluconate, lactate, salicylate, citrate, tartrate, ascorbate, succinate, maleate, fumarate, formate, benzoate, methanesulphonate, ethanesulphonate, benzenesulphonate and p-toluenesulphonate salts. Suitable base addition salts are formed from bases which form non-toxic salts and include the aluminium, calcium, lithium, magnesium, potassium, sodium, zinc and diethanolamine salts.

Preferably $R^1$ is CN or $C_{1-6}$ alkyl optionally substituted by one or more halogen atoms. More preferably, $R^1$ is CN, $CH_3$ or $CF_3$.

Preferably, Ar is A where A is optionally substituted phenyl, pyridyl, thienyl, furanyl, isoxazolyl, thiazolyl, isothiazolyl, oxazolyl or pyrroiyl, or Ar is AB where A is optionally substituted phenyl, pyridyl, thienyl, furanyl, isoxazolyl, thiazolyl, isothiazolyl, oxazolyl or pyrrolyl, and B is an optionally substituted dioxolo-, benzo-, pyrrolo-, pyrazolo-, furo-, thieno-, pyrido-, pyrazino-, pyridazino- or pyrimidino-moiety.

More preferably Ar is optionally substituted phenyl, methylenedioxyphenyl, naphthyl, pyridyl, thienyl, furanyl, isoxazolyl, thiazolyl, isothiazolyl, indolizinyl, isoindolyl, indolyl, indazolyl, quinolizinyl, quinolinyl, isoquinolinyl, phthalazinyly naphth,ridinyl, quinoxalinyl, quinazolinyl, cinnolinyl, oxazolyl, pyrrolyl, benzofurany or benzothienyl.

Further more preferably Ar is phenyl, 3,4-methylenedioxyphenyl, naphth-1-yl, pyridin-3-yl, pyridin-4-yl, thien-2-yl, thien-3-yl, furan-2-yl, furan-3-yl, thiazol-4-yl or isoxazol-5-yl, each optionally substituted by one or (independently) more halogen, $C_{1-6}$ alkyl optionally substituted by one or more halogen atoms, $C_{1-6}$ alkoxy optionally substituted by one or more halogen atoms, $C_{1-6}$ alkoxycarbonyl optionally substituted by one or more halogen atoms, $NO_2$, $NH_2$, CN or $S(O)_m(C_{1-6}$ alkyl optionally substituted by one or more halogen atoms).

A yet further more preferable group of compounds are those in which Ar is 4-methylphenyl, phenyl, 2-n-butylphenyl, 3-nitrophenyl, 4-bromophenyl, 4-chlorophenyl, 4-fluorophenyl, 3,5-dichlorophenyl, 2,3-dichlorophenyl, 3-chloro-4-fluorophenyl, 3-methoxycarbonylphenyl, 3-aminophenyl, 4-methoxyphenyl, 3,4-methylenedioxyphenyl, 3,4-dimethoxyphenyl, 3-fluorophenyl, 3-chlorophenyl, 2-fluorophenyl, 2-methoxyphenyl, 2-methylphenyl, 2-trifluoromethylphenyl, 2-chlorophenyl, naphth-1-yl, pyridin-3-yl, pyridin-4-yl, thien-2-yl, thien-3-yl, furan-2-yl, furan-3-yl, 3-bromoisoxazol-5-yl, 3-bromofiran-2-yl, 5-bromothien-2yl, 5-trifluoromethylthiothien-2-yl, 3,4-dibromoisoxazol-5-yl, 2-chlorofuran-3-yl, 2-bromofuran-3-yl, 3-chlorofuran-2-yl, 3-bromofuran-2-yl, 2-methylthiazol-4-yl, 2-trifluoromethylsulphinylfuran-3-yl, 2-trifluoromethylthiofuran-3-yl, 5-trifluoromethylfuran-3-yl, 5-trifluoromethylfuran-2-yl, 2,5-dichlorofuran-3-yl, 3-trifluoromethylfuran-2-yl and 2-trifluoromethylfuran-3-yl or 3-trifluoromethylthiofuran-2-yl.

Another subset (subset II) of preferred compounds are those in which Ar is A, where A is as defined above for compounds of formula (I), substituted with at least one substituent independently selected from halogen, $C_{1-6}$ alkyl optionally substituted by one or more halogen atoms, $C_{1-6}$ alkoxy optionally substituted by one or more halogen atoms, $C_{1-6}$ alkoxycarbonyl optionally substituted by one or more halogen atoms, $NO_2$, $NH_2$, CN or $S(O)_m(C_{1-6}$ alkyl optionally substituted by one or more halogen atoms), where there is a substituent at the position adjacent to the atom which forms a bond to the 4-position of the pyrazole.

More preferred among the subset II compounds are those in which Ar is phenyl, furan-2-yl, furan-3-yl, thien-2-yl, thien-3-yl or isoxazol-5-yl, substituted by one or (independently) more halogen, $C_{1-6}$ alkoxy optionally substituted by one or more halogen atoms, or $C_{1-6}$ alkyl optionally substituted by one or more halogen atoms or $S(O)_m(C_{1-6}$ alkyl optionally substituted by one or more halogen atoms), where there is a substituent at the position adjacent to the atom which forms a bond to the 4-position of the pyrazole.

Most preferably Ar is 2-n-butylphenyl, 2,3-dichlorophenyl, 2-fluorophenyl, 2-methoxyphenyl, 2-methylphenyl, 2-trifluoromethylphenyl, 2-chlorophenyl, 3-bromofuran-2-yl, 2-chlorofuran-3-yl, 2-bromofuran-3-yl, 3-chlorofuran-2-yl, 3-bromofiuran-2-yl, 2-trifluoromethylsulphinylfuran-3-yl, 2,5-dichlorofuran-3-yl, 3-trifluoromethylfuran-2-yl, 2-trifluoromethylfttran-3-yl, 3-trifluoromethylthiofuran-2-yl or 2-trifluoromethylthiofuran-3-yl.

Preferably $R^2$ is H or $NH_2$.

Preferably $R^3$ is halogen.

More preferably $R^3$ is Cl.

Preferably $R^4$ is H.

Preferably $R^5$ is H, $C_{1-6}$ alkyl optionally substituted by one or more halogen atoms, $C_{1-6}$ alkoxy optionally substituted by one or more halogen atoms or $SF_5$.

More preferably $R^5$ is H, $CH_3$, $CF_3$, $OCF_3$ or $SF_5$.

Preferably $R^6$ is H.

Preferably $R^7$ is halogen.

More preferably $R^7$ is Cl.

The compounds of the formula (I) may possess one or more asymmetric centres and so exist in two or more stereoisomeric forms. The present invention includes all the individual stereoisomers of the compounds of formula (I) and mixtures thereof. Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The compounds of the formula (I) provided by the invention can be prepared by the following Methods, and by the methods described in the Examples and Preparations section and suitable adaptation thereof, and where desired or necessary converted into a salt by conventional methods.

Method 1

The compounds of formula (I) can be prepared by palladium-catalysed cross-coupling reactions of compounds of the formula (II):

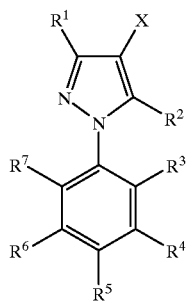

(II)

where $R^1$, $R^2$, $R^3$, $R^4$, $R^5$, $R^6$ and $R^7$ are as defined before for compounds of formula (I) and X is iodo or bromo, with boronic acids of the formula $ArB(OH)_2$, where Ar is as defined before for compounds of formula (I). The reaction is carried out using a suitable palladium (0) species such as $Pd(PPh_3)_4$, in a suitable solvent or solvent system such as N,N-dimethylformamide (DMF), ethanol/toluene/water, diglyme/water or dioxane/water, and using a suitable base such as $NaHCO_3$ or $K_2CO_3$. The general palladium-catalysed cross coupling chemistry is described by AR Martin and Y Yang in *Acta Chemica Scandinavica* (1993), 47, 221–230.

Intermediates of formula (II) above can be made by reaction of compounds of formula (III)

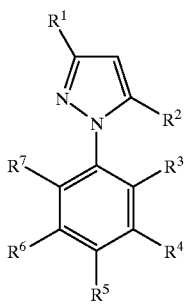

(III)

where $R^1$, $R^2$, $R^3$, $R^4$, $R^5$, $R^6$ and $R^7$ are as defined before for compounds of formula (I), with an iodinating or brominating species such as N-iodo- or N-bromosuccinimide in a suitable solvent such as acetonitrile.

Compounds of formula (III) can be made by conventional methods and by suitable adaptation of the methods described later in the Examples and Preparations section. Boronic acids of the formula $ArB(OH)_2$, where Ar is as defined before for compounds of formula (I) can be made by conventional methods and by suitable adaptation of the methods described later in the Examples and Preparations section.

Method 2

Compounds of formula (I) where Ar is 3-bromoisoxazol-5-yl and where $R^1$, $R^2$, $R^3$, $R^4$, $R^5$, $R^6$ and $R^7$ are as defined before for compounds of formula (I), can be made by reaction of compounds of the formula (TV):

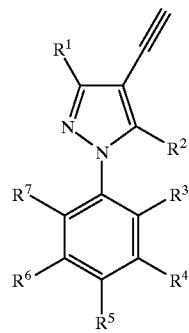

(IV)

where $R^1$, $R^2$, $R^3$, $R^4$, $R^5$, $R^6$ and $R^7$ are as defined before for compounds of formula (I), with dibromoformaldoxine and a suitable base such as $KHCO_3$, in a suitable solvent or solvent system such as water/ethyl acetate.

Compounds of formula (IV) can be made by conventional methods and those described in the Examples and Preparations section and suitable adaptation thereof Method 3

Compounds of the formula (I) where Ar is 3-(iodo, bromo, or chloro)furan-2-yl and $R^1$, $R^2$, $R^3$, $R^4$, $R^5$, $R^6$ and $R^7$ are as defined before for compounds of formula (I), i.e. compounds of formula (VIII) below where Y is iodo, bromo, or chloro, can be made according to the reaction sequence shown below:

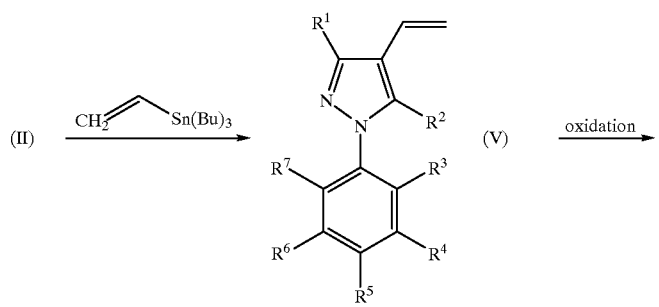

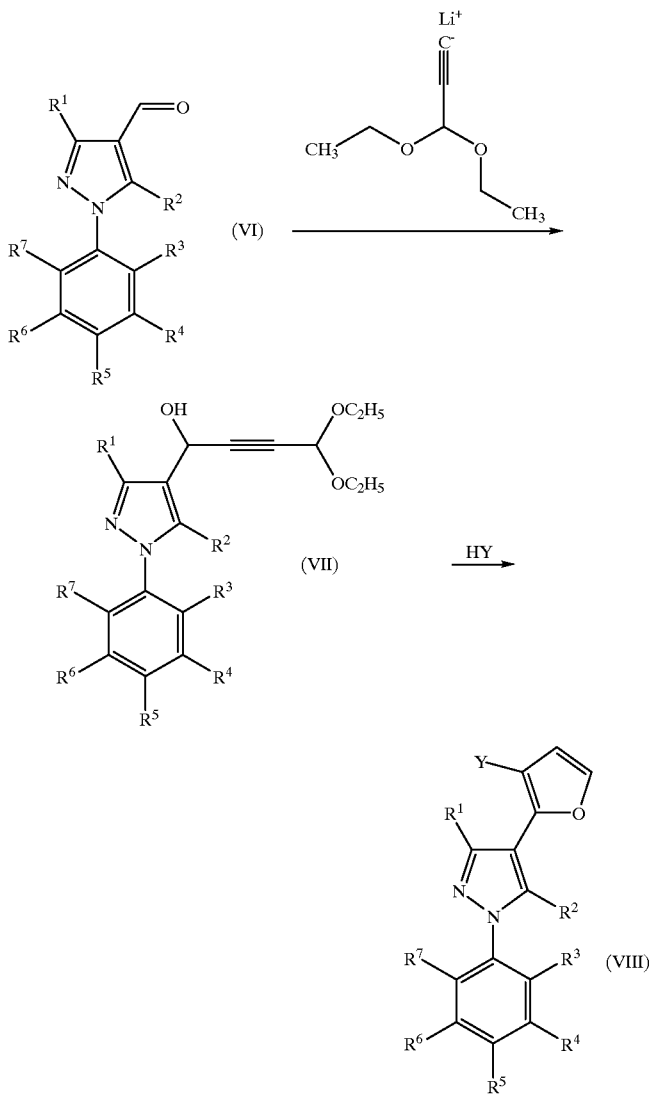

Preparation of compounds of formula (II) is described above in Method 1.

Compounds of formula (V) where $R^1$, $R^2$, $R^3$, $R^4$, $R^5$, $R^6$ and $R^7$ are as defined before for compounds of formula (I), can be made by reaction of compounds of formula (II) where $R^1$, $R^2$, $R^3$, $R^4$, $R^5$, $R^6$ and $R^7$ are as defined before for compounds of formula (I), with vinyltributylstannane in the presence of a palladium (0) catalyst. Preferably the catalyst is tetrakis(triphenylphosphine)palladium (0). The reaction is preferably carried out in a non-protic polar solvent such as dimethylformamide (DMF), and preferably at elevated temperatures such as about 75° C.

Compounds of formula (VI) where $R^1$, $R^2$, $R^3$, $R^4$, $R^5$, $R^6$ and $R^7$ are as defined before for compounds of formula (I), can be made by oxidising compounds of formula (II) where $R^1$, $R^2$, $R^3$, $R^4$, $R^5$, $R^6$ and $R^7$ are as defined before for compounds of formula (I), with a suitable oxidising regime such as with osmium tetroxide/N-methylmorpholine oxide (NN1O)/sodium metaperiodate. The reaction is carried out in a suitable solvent or solvent system such as acetone/water.

Compounds of formula (VII) where $R^1R^2$, $R^3$, $R^4$, $R^5$, $R^6$ and $R^7$ are as defined before for compounds of formula (I), can be made by reaction of aldehydes (VI) where $R^1$, $R^2$, $R^3$, $R^4$, $R^5$, $R^6$ and $R^7$ are as defined before for compounds of formula (I), with the lithium salt of propiolaldehyde diethyl acetal. Preferably the lithium salt of propiolaldehyde diethyl acetal is prepared in situ from propiolaldehyde diethyl acetal and a suitable lithiating agent such as n-butyllithium. The reaction is preferably carried out in an ether solvent such as tetrahydrofuran, and preferably under an inert atmosphere such as under dry nitrogen.

Compounds of formula (VIII) where $R^1$, $R^2$, $R^3$, $R^4$, $R^5$, $R^6$ and $R^7$ are as defined before for compounds of formula (I), and Y is chloro, bromo or iodo, can be made by reaction of compounds of formula (VII) where $R^1$, $R^2$, $R^3$, $R^4$, $R^5$, $R^6$ and $R^7$ are as defined before for compounds of formula (I), with an acid such as aqueous hydro(chloric, bromic or iodic) acid. The reaction can be carried out in a suitable solvent such as dioxane. The cyclisation reaction is derived from those described by Obrecht in *Helv.Chim.Acta*, vol.72 (1989) 447.

Method 4

Compounds of the formula (I) where Ar is 5-(iodo, bromo or chloro)thien-2-yl, and $R^1$, $R^2$, $R^3$, $R^4$, $R^5$, $R^6$ and $R^7$ are as defined before for compounds of formula (I), can be made by reacting the corresponding compound of formula (I) where Ar is thien-2-yl and $R^1$, $R^2$, $R^3$, $R^4$, $R^5$, $R^6$ and $R^7$ are as defined before for compounds of formula (I) (preparable by Method 1) with an iodinating, brominating or chlorinating species respectively such as the corresponding N-(iodo, bromo, or chloro)succinimide in a suitable solvent such as acetonitrile.

Method 5

Compounds of the formula (I) where Ar is 5-trifluoromethylsulphenylthien-2-yl, and $R^1$, $R^2$, $R^3$, $R^4$, $R^5$, $R^6$ and $R^7$ are as defined before for compounds of formula (I), can be made by reacting the corresponding compound of formula (I) where Ar is thien-2-yl and $R^1$, $R^2$, $R^3$, $R^4$, $R^5$, $R^6$ and $R^7$ are as defined before for compounds of formula (I) (preparable by Method 1) with trifluoromethylsulphenyl chloride and stannic chloride in a suitable solvent such as dichloromethane.

Method 6

Compounds of the formula (I) where Ar is 3-(iodo, bromo, or chloro)-4-(iodo, bromo, or chloro)-isoxazol-5-yl, and $R^1$, $R^2$, $R^3$, $R^4$, $R^5$, $R^6$ and $R^7$ are as defined before for compounds of formula (I), can be made by reacting the corresponding compound of formula (I) where Ar is 3-(iodo, bromo, or chloro)-isoxazol-5-yl and $R^1$, $R^2$, $R^3$, $R^4$, $R^5$, $R^6$ and $R^7$ are as defined before for compounds of formula (I) (preparable by Method 1 or 2) with an iodinating, brominating or chlorinating species respectively such as the corresponding N-(iodo, bromo, or chloro)succinimide in a suitable solvent such as acetonitrile.

Method 7

Compounds of the formula (I) where Ar is 2-(perfluoro-$C_{1-6}$ alky)furan-3-yl, $R^1$, $R^2$, $R^3$, $R^4$, $R^5$, $R^6$ and $R^7$ are as defined before for compounds of formula (I), can be made by reacting the corresponding compound of formula (I) where Ar is furan-3-yl and $R^1$, $R^2$, $R^3$, $R^4$, $R^5$, $R^6$ and $R^7$ are as defined before for compounds of formula (I) (preparable by Method 1) with (perfluoro-$C_{1-6}$ alkyl)-Z where Z is a suitable leaving group such as Br, I, Cl, etc. with sodium dithionite and disodium hydrogen phosphate in a suitable solvent such as DMF, under elevated pressure such as 1.37 bar to 3.1 bar (20 to 45 p.s.i.). This type of reaction is described in J.Chem.Soc., Perkin Transactions 2, (1990) 2293. (Perfluoro-$C_{1-6}$ alkyl)-Z compounds can be made by conventional methods.

Method 8

Compounds of the formula (I) where Ar is 2-(chloro or bromo)furan-3-yl, and $R^1$, $R^2$, $R^3$, $R^4$, $R^5$, $R^6$ and $R^7$ are as defined before for compounds of formula (I), can be made by reacting the corresponding compound of formula (I) where Ar is furan-3-yl and $R^1$, $R^2$, $R^3$, $R^4$, $R^5$, $R^6$ and $R^7$ are as defined before for compounds of formula (I) (preparable by Method 1) with chlorinating or brominating agents such as N-(chloro or bromo)succinimide, as appropriate, in a suitable solvent such as acetonitrile.

Method 9

Compounds of the formula (I) where Ar is 2-trifluoromethylsulphenylfuran-3-yl, and $R^1$, $R^2$, $R^3$, $R^4$, $R^5$, $R^6$ and $R^7$ are as defined before for compounds of formula (I), can be made by reacting the corresponding compound of formula (I) where Ar is furan-3-yl and $R^1$, $R^2$, $R^3$, $R^4$, $R^5$, $R^6$ and $R^7$ are as defined before for compounds of formula (I) (preparable by Method 1) with with trifluoromethylsulphenyl chloride and stannic chloride in a suitable solvent such as dichloromethane.

Method 10

Compounds of the formula (I) where $R^2$ is H, and $R^1$, Ar, $R^3$, $R^4$, $R^5$, $R^6$ and $R^7$ are as defined before for compounds of formula (I), can be made by reacting the corresponding compound where $R^2$ is $NH_2$ with an alkyl nitrite such as t-butyl nitrite, in a suitable solvent such as tetrahydrofuran (THF).

Method 11

Compounds of the formula (I) where $R^2$ is halogen and $R^1$, Ar, $R^3$, $R^4$, $R^5$, $R^6$ and $R^7$ are as defined before for compounds of formula (I), can be made by reacting reacting the corresponding compound where $R^2$ is $NH_2$ with an alkyl nitrite such as t-butyl nitrite, and a halide source such as iodine, tribromomethane or $CuCl_2$, in a suitable solvent such as tetrahydrofuran (THF).

Method 12

Compounds of the formula (I) where $R^2$ is $C_{1-6}$ alkyl and $R^1$, Ar, $R^3$, $R^4$, $R^5$, $R^6$ and $R^7$ are as defined before for compounds of formula (I), can be made by reacting reacting the corresponding compound where $R^2$ is iodine with a lithiating species such as n-butyllithiumn, to make the corresponding 5-lithiated, pyrazole, followed by reaction with an alkylating species ($C_{1-6}$ alkyl-Z) where Z is a suitable leaving group such as iodide or bromide.

Method 13

Compounds of the formula (I) where $R^2$ is $C_{2-6}$ alkenyl and $R^1$, Ar, $R^3$, $R^4$, $R^5$ $R^6$ and $R^7$ are as defined before for compounds of formula (I), can be made by reacting reacting the corresponding compound where R is iodine with a vinyltin species such as ($C_{2-6}$ alkenyl)Sn(n-butyl)$_3$. Preferably the reaction is carried out in the presence of a palladium catalyst, for exarnple tetrakis(triphenylphosphine)palladium (0). The reaction is preferably carried out in suitable solvent such as dimethylformamide, at or around 75° C. The ($C_{2-6}$ alkenyl)Sn(n-butyl)$_3$ Species can be made by conventional methods.

Method 14

Compounds of the formula (I) where $R^2$ is $C_{2-6}$ alkynyl and $R^1$, Ar, $R^3$, $R^4$, $R^5$, $R^6$ and $R^7$ are as defined before for compounds of formula (I), can be made by reacting reacting the corresponding compound where $R^2$ is iodine with an alkyne HCC(H or $C_{1-4}$ alkyl optionally substituted by one or more halogen).

Preferably the reaction is carried out in the presence of a palladium catalyst, for example bis(triphenylphosphine) palladium(II) chloride and cuprous iodide. The reaction is preferably carried out in suitable solvent which does not adversely affect the reaction, such as triethylamine and/or dimethylformamide, at or around room temperature. The alkyne can be made by conventional methods.

Compounds where $R^2$ is CC(chloro, bromo or iodo) and $R^1$, Ar, $R^3$, $R^4$, $R^5$, $R^6$ and $R^7$ are as defined before for compounds of formula (I), can be made from the corresponding compounds where $R^2$ is CCH by reaction with a halogenating species such as a N-(chloro, bromo or iodo) succinimide, in the presence of a silver(I) species such as $AgNO_3$ in a suitable solvent such as acetone.

Compounds Ahere $R^2$ is CC(fluoro) and $R^1$, Ar, $R^3$, $R^4$, $R^5$, $R^6$ and $R^7$ are as defined before for compounds of formula (I), can be made by standard elimination reactions well knon in the art of the corresponding compounds where $R^2$ is a suitable terminally-fluoro-substituted ethylenyl or ethyl moiety, such intermediates available by standard methods such as those mentioned herein and adaptation thereof using standard chemistry. Examples of such eliminations are dehydro(chlorin, bromin or iod)inations of the suitably substituted intermediates.

The compounds of the invention may be separated and purified by conventional methods. It will be apparent to those skilled in the art that sensitive functional groups may need to be protected and deprotected during synthesis of a compound of the invention. This may be achieved by conventional techniques, for example as described in "Protective Groups in Organic Synthesis" by T W, Greene and P G M Wuts, John Wiley and Sons Inc, 1991.

The compounds of the invention are useful because they possess parasiticidal activity in humans, animals and plants. They are particularly useful in the treatment of ectoparasites.

Dealing first with use of the compounds of the invention in humans, there is provided:

a) a pharmaceutical formulation comprising a compound of the invention in admixture with a pharmaceutically acceptable adjuvant, diluent or carrier which may be adapted for topical administration;

b) a compound of the invention, for use as a medicament;

c) the use of a compound of the invention in the manufacture of a parasiticidal medicament; and d) a method of treating a parasitic infestation in a patient which comprises administering an effective amount of a compound of the invention to the patient.

Turning now to the use of the compounds of the invention in non-human animals, the compounds may be administered alone or in a formulation appropriate to the specific use envisaged and to the particular species of host animal being treated and the parasite involyed. The methods by which the compounds may be administered include oral administration by capsule, bolus, tablet or drench, or as a pour-on or spot-on formulation, or alternatively, they can be administered by injection (e.g. subcutaneously, intramuscularly or intravenously), dip, spray, mousse, shampoo, powder, or as an implant.

It will be realised by those skilled in the art that similar formulations and dosages can be used in humans.

Such formulations are prepared in a conventional manner in accordance w ith standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolying or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolying or suspending the active ingredient in the liquid carrier such that the final formulation contains from 0.01 to 10% by weight of the active ingredient.

These formulations will vary with regard to the weight of active compound contained therein depending on the species of host animal to be treated, the severity and type of infection and the body weight of the host. For parenteral, topical (e.g. using pour-on or spot-on, dip, spray, mousse, shampoo or powder to deliver the compound) and oral administration, typical dose ranges of the active ingredient are 0.01–100 mg per kg of body weight of the animal. Preferably the range is 0.1 to 10 mg per kg.

As an alternative the compounds may be administered with the animal feedstuff and for this purpose a concentrated feed additive or premix may be prepared for mixing with the normal animal feed.

The compounds of the invention have utility in the control of arthropod, plant nematode, helminth or protozoan pests. The compounds of the invention may, in particular, be used in the field of veterinary medicine and livestock husbandry and in the maintenance of public health against arthropods, helminths or protozoa which are parasitic internally or externally upon vertebrates, particularly warn-blooded vertebrates, for example man and domestic animals, e.g. cattle, sheep, goats, equines, suine, poultry, dogs, cats and fish, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Orniithodorus moubata* and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,) Diptera (e.g. Aedes spp., Anopheles spp., Musca spp., Hypoderma spp., Gastrophilus spp., Simulium spp.); Hemiptera (e.g. Triatoma spp.); Phthiraptera (e.g. Damalinia spp., Linoqnathus spp.) Siphonaptera (e.g. Ctenocephalides spp.); Dictyoptera (e.g. Periplaneta spp., Blatella spp.); Hymenoptera (e.g. *Monomoriuni pharaonis*); for example against infections of the gastrointestinal tract caused by parasitic nematode worms, for example members of the family Trichostrongylidae, *Nippostronylus brasiliensis, Trichinella spiralis, Haemonchus contortus, Trichostronylus colubriformis, Nenzatodirus battus, Ostertagia circumcincta, Trichostrongylus axei,* Cooperia spp. and *Hymenolepis nana*, in the control and treatment of protozoal diseases caused by, for example Eimeria spp. e.g. *Eimeria tenella, Eimeria acervulina, Eimeria brunetti, Eimeria maxima, Eimeria necatrix, Eimeria bovis, Eimeria zuerni* and *Eimeria ovinoidalis; Trypanosomia cruzi*, Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal foodstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptoterms spp.; in agriculture, against adults, larvae and eggs of Lepidoptera (butterflies and moths), e.g. Heliothis spp. such as Heliothis virescens (tobacco budworm), *Heliothis armioera* and *Heliothis zea*, Spodoptera spp. such as *S. exemipta*,

*S. littoralis* (Egyptian cotton worm), *S. eridania* (southern army wormn), *Mamiestra configurata* (bertha army worm); Earias spp. e.g. *E. insulana* (Egyptian bollworn), Pectinophora spp. e.g. *Pectinophora gossypiella* (pink bollworm), Ostrinia spp. such as O. nubilalis (European comborer), Trichoplusia *ni* (cabbage looper), Pieris spp. (cabbage worms), Laphyqma spp. (army worms), Agrotis and Amathes spp. (cutworms). Wiseana spp. (porina moth), Chilo spp. (rice stem borer), Tryporyza spp. and Diatraea spp. (sugar cane borers and rice borers), Sparganothis *pilleriania* (grape berry moth), Cydia pomonella (codling moth), Archips spp. (fruit tree tortrix moths), *Plutella xylostella* (diamond black moth); against adult and larvae of Coleoptera (beetles) e.g. *Hypathenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryophilus* (rice water weevil), Melioethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp.; Nymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci*: Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dernaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphacotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meliodogyne spp. (e.g. *M. incognita*); cyst nematodes such as Globodera spp. (e.g. *G. rostochiensis*); Heterodera spp. (e.g. H. avenae); Radopholus spp. (e.g. *R. similis*); lesion nematodes such as Pratylenchus spp. (e.g. *P. pratensis*), Belonolianus spp. (e.g. *B. giacilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. T. primtiveius); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritziema-bosi, A. besseyi*); stem and bulb eelw‚orms such as Ditylenchus spp. (e.g. *D. dipsaci*).

The compounds of the invention also have utility in the control of arthropod or nematode pests of plants. The active compound is generally applied to the locus in which arthropod or nematode infestation is to be controlled at a rate of about 0.005 kg to about 25 kg of active compound per hectare of locus treated, preferably 0.02 to 2 kg/ha. Under ideal conditions, depending on the pest to be controlled, the lower rate may offer adequate protection. On the other hand, adverse weather conditions, resistance of the pest and other factors may require that the active ingredient be used in higher proportions. For foliar application, a rate of 0.01 to 1 kg/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of the invention may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of the invention are of value in controlling pests which feed on parts of the plant remote from the point of application, e.g. leaf feeding insects are killed by the subject compounds applied to roots. In addition the compounds may reduce attacks on the plant by means of antifeeding or repellent effects.

The compounds of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of the invention are of value in the control or arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

According to a further aspect of the invention, there is provided a parasiticidal formulation comprising a compound of the invention, in admixture with a compatible adjuvant, diluent or carrier. Preferably, the formulation is adapted for topical administration.

The invention further provides a compound of the invention for use as a parasiticide; and a method of treating a parasitic infestation at a locus, which comprises treatment of the locus with an effective amount of a compound of the invention. Preferably, the locus is the skin or fur of an animal, or a plant surface or the soil around the plant to be treated.

It is to be appreciated that reference to treatment includes prophylaxis as well as the alleviation of established symptoms of a parasitic infection.

Test for Insecticidal Activity

Adult flies (*Stomoxys calcitrans*) are collected and anaesthetized using $CO_2$. 1 µl of an acetone solution containing the test compound is applied directly to the thorax of the fly. Flies are then placed carefully into a 50 ml tube covered kth damp gauze to recover from the $CO_2$. Negative controls have 1 µl of acetone dispensed onto them. Mortality is assessed 24 hours after dosing.

Thus the invention further provides:
 the processes described herein for preparing the compounds of formula (I) and salts thereof;
 pharmaceutical, veterinary or crop parasiticidal formulations comprising a compound of formula (I), or a pharmaceutically- or veterinarily-acceptable salt thereof, in admixture with a compatible adjuvant, diluent or carrier;
 compounds of formula (I), without proviso, and pharmaceutically- or veterinarily-acceptable salts, and formulations thereof, for use as a medicament;
 a method of treating a parasitic infestation at a locus which comprises treating the locus with an effectine amount of a compound of formula (I), without proviso, or a salt thereof, or formulation thereof,
 the use of a compound of formula (I), without proviso, or pharmaceutically- or veterinarily-acceptable salt thereof, or formulation thereof, in the manufacture of a medicament for the treatment of a parasitic infestation; and
 any novel intermediates described herein.

The invention is illustrated by the following, Examples. In the Examples and Preparations, melting points were determined using a Gallenkamp melting point apparatus and are uncorrected. Nuclear magnetic resonance (IM) data were obtained using a Bruker AC300 or AM300 and are quoted in parts per million using solvent or tetramethylsilane as reference. Mass spectral (MS) data were obtained on a Finnigan Mat. TSQ 7000 or a Fisons Instruments Trio 1000. The calculated and observed ions quoted refer to the isotopic composition of lowest mass. HPLC purification was performed on a 21×250 mm Dynamax™ 5µl ODS reverse-phase column eluted at 10 ml/minute with acetonitrile: 0.005M aqueous heptanesulphonic acid methanol (50:40:10). Fractions were processed by evaporation of the non-aqueous components followed by partition between ether and saturated aqueous sodium hydrogen carbonate solution. The organic layer was then separated, dried and evaporated.

The compound of Example A3 was found to produce 100% mortality in the dosage range 100–0.1 µg per fly.

EXAMPLES AND PREPARATIONS

Preparation 1: 5-Amino-3-cyano-1-(2,6dichloro-4-trifluoromethylphenyl)pyrazole, used in example A1, was prepared as described in EP-295,117 A1.

Preparation 2: 5-Amino-3-cyano-1-(2,6-dichloro-4-metbhlphenyl)pyrazole, used in Example A29, was prepared by the method of Preparation 1 substituting 2.6-dichiloro-4-methylaniline for 2.6-dichloro-4-trifluoromethylaniline.

Preparation 3: 5-Amino-3-cyano-1-(2,6-dichlorophenNl) pyrazole, used in Example A30, was prepared by the method of Preparation 1 substituting 2,6-dichloroaniline for 2,6-dichloro-4-trifluoromethylaniline.

Preparation 4: 3-Fluorophenylboronic acid (and other boronic acids)

To a stirred solution of 1-bromo-3-fluorobenzene (0.05M) in anhydrous ether (130 ml) at –78° C. under an atmosphere of dry nitrogen was added dropw-ise n-butyllithium (0.52M, of a 2.5M solution in hexane) at such a rate that the temperature of the reaction mixture did not exceed –73° C. (~15 minutes required for the addition). The reaction mixture was stirred for 20 minutes and then tri-isopropyl borate (0.1M) was added at such a rate that the temperature of the reaction mixture did not exceed –65° C. The reaction mixture was stirred for 60 minutes and then allowed to warm to room temperature after which it was poured into ether (100 ml) and dilute aqueous hydrochloric acid (150 ml, prepared by tenfold aqueous dilution of concentrated hydrochloric acid). The aqueous layer was separated and extracted with ether (100 ml). The combined ether layers were washed with water (75 ml), dried ($Na_2SO_4$) and evaporated. The residue was triturated with hexane (40 ml) to produce, after removal of the mother liquor, a white solid which was used without further purification.

Other boronic acids not commercially available nor described in the chemical literature were prepared by the method described above for 3-fluorophenylboronic acid substituting an appropriate aryl halide for 1-bromo-3-fluorobenzene.

Preparation 5: 2,4,6-Tri(n-butylphenyl)boroxin

The method of Preparation 4 employing 2-bromo-n-butylbenzene and t-butyllithium yielded the anhydride, 2,4,6-tri(n-butylphenyl)boroxin.

Preparation A1

5-Amino-3-cyano-1-(2,6dichloro-4-trifluoromethylphenyl)-4-iodopyrazole

To a stirred solution of 5-amino-3-cyano-1-(2.6-dichloro-4-trifluoromethylphenyl)pyrazole (prepared as described in EP 295 117 A1) (5.0 g) in acetonitrile (60 ml) at room temperature was added N-iodosuccinimide (3.52 g), portion-wise over a period of five minutes. Stirring was continued for 1 hr and the mixture was then evaporated to dryness to provide the crude product (8.2 g), still containing succinimide. This may be used without further purification or, if desired, purified by partitioning between dichloromethane and water, separating, drying ($MgSO_4$) and evaporating the organic layer to produce a yellow solid. Trituration with hexane provided the title compound as a white solid, m.p. 213° C. (decomp.).

Example A2

5-Amino-3-cyano-1-(2,6dichloro-4-trifluoromethylphenyl)-4-(4-methylphenyl)pyrazole To a rapidly stirred solution of 5-amino-3-cyano-1-(2,6-dichloro-4-trifluoromethylphenyl)-4-iodopyrazole (0.45 g) in toluene (2 ml) containing tetrakis(triphenylphosphine) palladium(0) (0.02 g) was added saturated aqueous sodium hydrogen carbonate solution (1 ml) and a solution of 4-methylphenylboronic acid (0.3 g) in ethanol (1 ml). The mixture was heated under reflux for 2 hours. After cooling the organic layer was separated, dried ($MgSO_4$) and evaporated. The residue was taken up the minimum amount of ethyl acetate and purified by column chromatography on silica gel (50 g) eluted with dichloromethane. Combination and evaporation of suitable fractions followed by trituration with hexane gave the title compound as an off-white crystalline solid, m.p.243–4° C.

NMR($CDCl_3$): 2.42(s, 3H), 3.87 (br. s, 2H), 7.33 (d, 2H), 7.44 (d, 2H), 7.82 (s, 2H). MS (themospray): M/Z [M+H] 411.1; $C_{18}H_{11}Cl_2F_3N_4$+H requires 411.04.

Example A3

5-Amino-3-cyano-1-(2,6-dichloro-4-trifluoromethylphenyl)-4-phenylpyrazole

To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of phenylboronic acid (0.1 g) in ethanol (1 ml). The mixture was heated under reflux for 1 hour, then left at room temperature overnight and then poured into ether (25 ml) and water (25ml). The organic layer was separated, dried ($MgSO_4$) and evaporated. The residue was taken up the minimum amount of ethyl acetate and purified by column chromatography on silica gel (20 g) eluted with dichloromethane hexane (1:1). Combination and evaporation of suitable fractions followed by recrystallisation from ether/hexane gave the title compound as a white solid, m.p. 198–9° C.

NMR($CDCl_3$): 3.9 (br. s, 2H), 7.4 (m, 1H), 7.52 (m, 4H), 7.82 (s, 2H). MS (thermospray): M/Z [M+H] 397.1; $C_{17}H_9Cl_2F_3N_4$+H requires 397.02.

Example A4

5-Amino-3-cyano-1-(2,6-dichloro-4-trifluoromethylphenyl)-4-(3-nitrophenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 3-nitrophenylboronic acid (0.21 g) in ethanol (1 ml). The mixture was heated under reflux for 1 hour, then left at room temperature overnight and then poured into ether (25 ml) and water (25 ml). The organic layer was separated, dried ($MgSO_4$) and evaporated. The residue was taken up the minimum amount of ethyl acetate and purified by column chromatography on silica gel (20 g) eluted with dichloromethane:hexane (1:1). Combination and evaporation of suitable fractions followed by recrystallisation from ether/hexane gave the title compound as an pale yellow solid m.p. 212–4° C.

NMR($CDCl_3$): 4.02 (br. s, 2H), 7.75 (t, 1H), 7.86 (s, 2H), 7.98 (dd, 1H), 8.26 (dd, 1H), 8.41 (dd, 1H). MS (thermospray): M/Z [M+$NH_4$] 459.2; $C_{17}H_8Cl_2F_3N_5O_2$+$NH_4$ requires 459.03.

Example A5

5-Amino-4-(4-bromophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 4-bromophenylboronic acid (0.25 g) in ethanol (1 ml). The mixture was heated under reflux for 1 hour, then left at room temperature overnight and then poured into ether (25 ml) and water (25 ml). The organic layer was separated, dried ($MgSO_4$) and evaporated. The residue was taken up the minimum amount of ethyl acetate and purified by column chromatography on silica gel (20 g) eluted with dichloromethane: hexane (1:1). Combination and evaporation of suitable fractions followed by recrystallisation from ether/hexane gave the title compound as an off-white solid, m.p. 242–4° C.

NMR($CDCl_3$): 3.9 (br. s, 2H), 7.43 (d, 2H), 7.64 (d, 2H), 7.82 (s, 2H). MS (thermnospray): M/Z [M+H] 474.7; $C_{17}H_8BrCl_2F_3N_4$+H requires 474.9.

Example A6

5-Amino-4-(4-chlorophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 4-chlorophenylboronic acid (0.20 g) in ethanol (1 ml). The mixture was heated under reflux for 3 hours, then left at room temperature overnight and then poured into ether (25 ml) and water (25 ml). The organic layer was separated, dried ($MgSO_4$) and evaporated. The residue was taken up the minimum amount of ethyl acetate and purified by column chromatography on silica gel (20 g) eluted with dichloromethane:hexane (1:2). Combination and evaporation of suitable fractions followed by recrystallisation from ether/hexane gave the title compound as an off-white solid, m.p. 235–7° C.

NMR($CDCl_3$): 3.9 (br. s, 2H), 7.5 (s, 4H), 7.82 (s, 2H). MS (thermospray): M/Z [M+H] 430.8; $C_{17}H_8Cl_3F_3N_4$+H requires 430.98.

Example A7

5-Amino-3-cyano-1-(2,6-dichloro-4-trifluoromethylphenyl)-4-(4-fluorophenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 4-fluorophenylboronic acid (0.17 g) in ethanol (1 ml). The mixture was heated under reflux for 1 hour, then left at room temperature overnight and then poured into ether (25 ml) and water (25 ml). The organic layer was separated, dried ($MgSO_4$) and evaporated. The residue was taken up the minimum amount of ethyl acetate and purified by column chromatography on silica gel (20 g) eluted with dichloromethane:hexane (1:1). Combination and evaporation of suitable fractions followed by recrystallisation from ether/hexane gave the title compound as a white solid, m.p. 222–3° C.

NMR(CDCl$_3$): 3.87 (br. s, 2H), 7.22 (m, 2H), 7.54 (m, 2H), 7,82 (s, 2H). MS (thermospray): M/Z [M+H] 415.0; C$_{17}$H$_8$Cl$_2$F$_4$N$_4$+H requires 415.01.

Example A8

5-Amino-3-cyano-4-(3,5-dichloropbenyl)-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) wAas added saturated aqueous sodium hydrogen carbonate solution (1 ml) and a solution of 3,5-dichlorophenylboronic acid (0.24 g) in ethanol (1 ml). The mixture was heated under reflux for 3 hours, then left at room temperature overnight and then poured into ether (25 ml) and water (25 ml). The organic layer was separated, dried (MgSO$_4$) and evaporated. The residue was taken up the minimum amount of ethyl acetate and purified by column chromatography on silica gel (20 g) eluted with dichloromethane:hexane (1:2). Combination and evaporation of suitable fractions followed by recrystallisation from ether/hexane gave the title compound as a white solid, m.p. 228–30° C.

NMR(CDCl$_3$): 3.92 (br. s, 2H), 7.38 (d, 1H), 7.43 (d, 2H), 7.82 (s, 2H). MS (thermospray): M/Z [M+H] 464.7; C$_{17}$H$_7$Cl$_4$F$_3$N$_4$+H requires 464.9.

Example A9

5-Amino-4-(3-chloro-4-fluorophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 3-chloro-4-fluorophenylboronic acid (0.22 g) in ethanol (1 ml). The mixture was heated under reflux for 3 hours, then left at room temperature overnight and then poured into ether (25 ml) and water (25 ml). The organic layer was separated, dried (MgSO$_4$) and evaporated. The residue was taken up the minimum amount of ethyl acetate and purified by column chromatography on silica gel (20 g) eluted with dichloromethane:hexane (1:2). Combination and evaporation of suitable fractions followed by recrystallisation from ether/hexane gave the title compound as an off-white solid, m.p. 197–8° C.

NMR(CDCl$_3$): 3.9 (br. s, 2H), 7.3 (t, 1H), 7.45 (m, 1H), 7.59 (dd, 1H), 7.82 (s, 2H). MS (thermospray): M/Z [M+H] 448.9; C$_{17}$H$_7$Cl$_3$F$_4$N$_4$+H requires 448.98.

Example A10

5-Amino-3-cyano-1-(2,6-dichloro-4-trifluoromethylphenuyl)-4-(3-methoxycarbonylphenyl)pyrazole To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 3-methoxycarbonylphenylboronic acid (0.158 g) in ethanol (1 ml). The mixture was heated under reflux for 2 hours, then left at room temperature overnight and then poured into ether (25 ml) and water (25 ml). The organic layer was separated, dried (MgSO$_4$) and evaporated. The residue was taken up the minimum amount of ethyl acetate and purified by column chromatography on silica gel (20 g) eluted with dichloromethane:hexane (1:1). Combination and evaporation of suitable fractions followed by recrystallisation from ether/hexane gave the title compound as an light brown solid, m.p. 214–6° C.

NMR(CDCl$_3$): 3.95 (s+br. s, 5H), 7.6 (t, 1H), 7.79 (d, 1H), 7.80 (s, 2H), 8.05 (d, 1H), 8.09 (s, 1H). MS (thermospray): M/Z [M+NH$_4$] 472.2; C$_{19}$H$_{11}$Cl$_2$F$_3$N$_4$O$_2$+NH$_4$ requires 472.06.

Example A11

5-Amino-4-(3-aminophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.447 g) in toluene (2 ml) containing tetrakis(triphenylphosphine) palladium(0) (0.02 g) was added saturated aqueous sodium hydrogen carbonate solution (1 ml) and a solution of 3-aminophenylboronic acid (0.310 g) in ethanol (1 ml). The mixture was heated under reflux for 3 hours, then left at room temperature overnight. Saturated aqueous sodium hydrogen carbonate solution (0.5 ml) and tetrakis (triphenylphosphine)palladium(0) (0.01 g) were added and the mixture heated under reflux for 3 hours. The cooled reaction mixture was then poured into ether (25 ml) and water (25 ml). The organic layer was separated, dried (MgSO$_4$) and evaporated. The residue was purified by column chromatography on silica gel (40 g) eluted with dichloromethane methanol (0→1%). Combination and evaporation of suitable fractions gave the title compound as a pale brown crystalline solid, m.p. 187° C.

NMR(CDCl$_3$): 2.8 (br. s, 2H), 3.94 (br. s, 2H), 6.7 (d, 1H), 6.87 (s, 1H), 6.89 (d, 1H), 7.28 (dd, 1H), 7.8 (s, 2H). MS (thermospray): M/Z [M+H] 412.1; C$_{17}$H$_{10}$Cl$_2$F$_3$N$_5$+H requires 412.03.

Example A12

5-Amino-3-cyano-1-(2,6-dichloro-4-trifluoromethylpbenyl)-4-(4-metboxyphenyl)pyrazole To a rapidly stirred solution of 5-amino-3-cyano-1-(2,6-dichloro-4-trifluoromethylphenyl)-4-iodopyrazole (0.447 g) in toluene (2 ml) containing tetrakis(triphenylphosphine) palladium(0) (0.02 g) was added saturated aqueous sodium hydrogen carbonate solution (1 ml) and a solution of 4-methoxyphenylboronic acid (0.302 g) in ethanol (1 ml). The mixture was heated under reflux for 2.75 hours, then left at room temperature overnight. Saturated aqueous sodium hydrogen carbonate solution (0.5 ml) and tetrakis (triphenylphosphine)palladium(0) (0.01 g) were added and the mixture heated under reflux for 3 hours. The cooled reaction mixture was then poured into ether (25 ml) and water (25 ml). The organic layer was separated, dried (MgSO$_4$) and evaporated. The residue was purified by column chromatography on silica gel (50 g) eluted with dichloromethane. Combination and evaporation of suitable fractions gave the title compound as an off-white crystalline solid, m.p. 222° C. with softening at 192° C.

NMR(CDCl$_3$): 3.88 (s+br. s, 5H), 7.06 (d, 2H), 7.47 (d, 2H), 7.81 (s, 2H). MS (thermospray): M/Z [M+H] 427.4; C$_{18}$H$_{11}$Cl$_2$F$_3$N$_4$O+H requires 427.03.

Example A13

5-Amino-3-cyano-1-(2,6-dichloro-4-trifluoromethylphenyl)-4-(3,4-methylenedioxyphenyl)pyrazole To a rapidly stirred solution of 5-amino-3-cyano-1-(2,6-dichloro-4-trifluoromethylphenyl)-4-iodopyrazole (0.894 g) in toluene (4 ml) containing tetrakis(tnrphenylphosphine) palladium(0) (0.04 g) was added saturated aqueous sodium hydrogen carbonate solution (3 ml) and a solution of 3.4-methylenedioxypheny,lboronic acid (0.600 g) in ethanol (2 ml). The mixture was heated under reflux for 4 hours, cooled and then poured into ether (40 ml) and water (40 ml). The organic layer was separated, washed with water (2×30 ml), brine (30 ml) and then dried (MgSO$_4$) and evaporated. The residue %as purified by column chromatography on silica gel (30 g) eluted with dichloromethane. Combination and evaporation of suitable fractions gave the title compound as a pale brown crystalline solid, m.p. 222° C. with softening at 198° C.

NMR(CDCl$_3$): 3.86 (br. s, 2H), 6.03 (s, 2H), 6.86 (d, 1H), 6.9 (m, 2H), 7.81 (s, 2H). MS (thermospray): M/Z [M+H] 440.7; C$_{18}$H$_9$Cl$_2$F$_3$N$_4$O$_2$+H requires 441.01.

Example A14

5-Amino-3-cyano-1-(2,6-dichloro-4-trifluoromethylphenyl)-4-(3,4-dimethoxyphenyl)pyrazole To a rapidly stirred solution of 5-amino-3-cyano-1-(2,6-dichloro-4-trifluoromethylphenyl)-4-iodopyrazole (0.335 g) in toluene (2 ml) containing tetrakis(triphenylphosphine) palladium(0) (0.03 g) was added saturated aqueous sodium hydrogen carbonate solution (1 ml) and a solution of 3,4-dimethoxyphenylboronic acid (0.273 g) in ethanol (1 ml). The mixture was heated under reflux for 5 hours, cooled and then poured into ether (25 ml) and water (25 ml). The organic layer was separated, washed with water (2×25 ml), brine (25 ml) and then dried (MgSO$_4$) and evaporated. The residue was purified by column chromatography on silica gel (30 g) eluted with dichloromethane: ethanol (99:1). Combination and evaporation of suitable fractions gave the title compound as a pale pink crystalline solid, m.p. 250° C.

NMR(CDCl$_3$): 3.88 (br. s, 2H), 3.94 (s, 3H), 3.97 (s, 3H), 6.99 (d, 1H), 7.01 (m, 2H), 7.81 (s, 2H). MS (thermospray): M/Z [M+H] 457.0; C$_{19}$H$_{13}$Cl$_2$F$_3$N$_4$O$_2$+H requires 457.05.

Example A15

5-Amino-3-cyano-1-(2,6-dichloro-4-trifuoromethylphenyl)-4-(3-fluorophenyl)pyrazole To a rapidly stirred solution of 5-amino-3-cyano-1-(2,6-dichloro-4-trifluoromethylphenyl)-4-iodopyrazole (0.335 g) in toluene (2 ml) containing tetrakis(triphenylphosphine) palladium(0) (0.03 g) was added saturated aqueous sodium hydrogen carbonate solution (1 ml) and a solution of 3-fluorophenylboronic acid (0.210 g) in ethanol (1 ml). The mixture was heated under reflux for 6 hours, cooled and then poured into ether (25 ml) and water (25 ml). The organic layer was separated, washed with water (25 ml), brine (25 ml) and then dried (Na$_2$SO$_4$) and evaporated. The residue was purified by column chromatography on silica gel (50 g) eluted with dichloromethane:ethanol (99:1). Combination and evaporation of suitable fractions gave a pale yellow solid (0.22 g) which was further purified by HPLC. Combination and processing of suitable fractions gave the title compound as an white crystalline solid, m.p. 164° C.

NMR(CDCl$_3$): 3.96 (br. s, 2H), 7.04 (m, 1H), 7.13 (m, 1H), 7.18 (m, 1H), 7.24 (m, 1H), 7.81 (s, 2H). MS (thermospray): M/Z [M+H] 415.0; C$_{17}$H$_8$Cl$_2$F$_4$N$_4$+H requires 415.01.

Example A16

5-Amino-4-(3-chlorophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.335 g) in toluene (2 ml) containing tetrakis(triphenylphosphine) palladium(0) (0.03 g) was added saturated aqueous sodium hydrogen carbonate solution (1 ml) and a solution of 3-chlorophenylboronic acid (0.240 g) in ethanol (1 ml). The mixture wAas heated under reflux for 4 hours, cooled and then poured into ether (25 ml) and water (25 ml). The organic layer was separated, washed with water (25 ml), brine (25 ml) and then dried (Na$_2$SO$_4$) and evaporated. The residue was purified by column chromatography on silica gel (40 g) eluted with dichloromethane. Combination and evaporation of suitable fractions gave a white solid (70 mg) which was further purified by HPLC. Combination and processing of suitable fractions gave the title compound as a white crystalline solid, m.p. 161–2° C.

NMR(CDCl$_3$): 3.94 (br.s, 2H), 7.38 (m, 1H), 7.47 (m, 2H), 7.51 (m, 1H), 7.81 (s, 2H). MS (thermospray) M/Z [M+H] 431.1; C$_{17}$H$_8$Cl$_3$F$_3$N$_4$+H requires 430.98.

Example A17

5-Amino-3-cyano-1-(2,6-dichloro-4-trifluoromethylphenyl)-4-(2-fluorophenyl)pyrazole To a rapidly stirred solution of 5-amino-3-cyano-1-(2,6-dichloro-4-trifluoromethylphenyl)-4-iodopyrazole (0.335 g) in toluene (2 ml) containing tetrakis(triphenylphosphine) palladium(0) (0.03 g) was added saturated aqueous sodium hydrogen carbonate solution (1 ml) and a solution of 2-fluorophenylboronic acid (0.210 g) in ethanol (1 ml). The mixture was heated under reflux for 5.5 hours, cooled and then poured into ether (25 ml) and water (25 ml). The organic layer was separated, washed with water (25 ml), brine (25 ml) and then dried (Na$_2$SO$_4$) and evaporated. The residue was purified by column chromatography on silica gel (40 g) eluted with dichloromethane. Combination and evaporation of suitable fractions gave the title compound as a white crystalline solid, m.p. 197° C.

NMR(CDCl$_3$): 3.9 (br. s, 2H), 7.18 (m, 2H), 7.4 (m, 1H), 7.6 (m, 1H), 7.81 (s, 2H). MS (thermospray): M/Z [M+H] 415.0; C$_{17}$H$_8$Cl$_2$F$_4$N$_4$+H requires 415.01.

Example A18

5-Amino-3-cyano-1-(2,6-dichloro4-trifluoromethylphenyl)-4-(2-methoxyphenyl)pyrazole To a rapidly stirred solution of 5-amino-3-cyano-1-(2,6-dichloro-4-trifluoromethylphenyl)-4-iodopyrazole (1 g) in toluene (6 ml) containing tetrakis(triphenylphosphine) palladium(0) (0.09 g) was added saturated aqueous sodium hydrogen carbonate solution (7 ml) and a solution of 2-methoxypbenylboronic acid (1.7 g) in ethanol (3 ml). The mixture was heated under reflux for 2.5 hours, cooled and then poured into ether (60 m) and water (50 ml). The layers were separated and the aqueous phase extracted with a second portion of ether (60 ml). The combined organic layers were washed with water (2×45 ml). brine (40 ml) and then dried ($Na_2SO_4$) and evaporated. The residue was purified by column chromatography on silica gel (60 g) eluted with ether:hexane (3:2). After combination and evaporation of suitable fractions the residue was further purified by HPLC. Combination and processing of suitable fractions gave the title compound as a white crystalline solid, m.p. 193° C.

NMR($CDCl_3$): 3.89 (s, 3H), 3.91 (br. s, 2H), 7.0 (d, 1H), 7.09 (t, 1H), 7.37 (dd, 1H), 7.5 (d, 1H), 7.78 (s, 2H). MS (thermospray): M/Z [M+H] 427.0; $C_{18}H_{11}Cl_2F_3N_4O$+H requires 427.03.

Example A19

5-Amino-3-cyano-1-(2,6-dichloro-4-trifluoromethylphenyl)-4-(2-methylphenyl)pyrazole To a rapidly stirred solution of 5-amino-3-cyano-1-(2,6-dichloro-4-trifluoromethylphenyl)-4-iodopyrazole (1 g) in toluene (6 ml) containing tetrakis(triphenylphosphine) palladium(0) (0.05 g) was added saturated aqueous sodium hydrogen carbonate solution (3 ml) and a solution of 2-methylphenylboronic acid (0.610 g) in ethanol (3 ml). The mixture was heated under reflux for 24 hours, cooled and then poured into ether (60 ml) and water (80 ml). The layers were separated and the aqueous phase extracted with a second portion of ether (60 ml). The combined organic layers were washed with water (2×50 ml), brine (50 ml) and then dried ($MgSO_4$) and evaporated. The residue was purified by column chromatography on silica gel (50 g) eluted with ether:hexane (3:2). Combination and evaporation of suitable fractions gave the title compound as a pale brown crystalline solid, m.p. 199–202° C.

NMR($CDCl_3$): 2.32 (s, 3H), 3.62 (br. s, 2H), 7.33 (m, 4H), 7.81 (s, 2H). MS (thermospray): M/Z [M+H] 411.0; $C_{18}H_{11}Cl_2F_3N_4$+H requires 411.04.

Example A20

5-Amino-3-cyano-1-(2,6-dichloro-4-trifluoromethylphenyl)-4-(2-trifluoromethlphenyl)pyrazole To a rapidly stirred solution of 5-amino-3-cyano-1-(2,6-dichloro-4-trifluoromethylphenyl)-4-iodopyrazole (0.62 g) in toluene (5 ml) containing tetrakis(triphenylphosphine) palladium(0) (0.056 g) was added saturated aqueous sodium hydrogen carbonate solution (5 m) and a solution of 2-trifluoromethylphenylboronic acid (1.32 g) in ethanol (2.5 ml). The mixture was heated under reflux for 1.5 hours, cooled and then poured into ether (60 ml) and water (50 ml). The layers were separated and the aqueous phase extracted with a second portion of ether (60 ml). The combined organic layers were washed with water (2×40 ml), brine (40 ml) and then dried ($Na_2SO_4$) and evaporated. The residue was purified by column chromatography on silica gel (50 g) eluted with dichloromethane. Combination and evaporation of suitable fractions gave the title compound as a white crystalline solid, m.p. 210–2° C.

NMR($CDCl_3$): 3.57 (br. s, 2H), 7.49 (d, 1H), 7.6 (m, 1H), 7.69 (m, 1H), 7.81 (s, 2H), 7.83 (m, 1H). MS (thermospray): MIZ [M+H] 465.0; $C_{18}H_8Cl_2F_6N_4$+H requires 465.01.

Example A21

5-Amino-4-(2-chlorophenyl)-3-cyano-1-(2,6-dichloro-4-trifluoromethylphenyl)pyrazole To a rapidly stirred solution of 5-amino-3-cyano-1-(2,6-dichloro-4-trifluoromethylphenyl)-4-iodopyrazole (0.31 g) in toluene (2 ml) containing tetrakis(triphenylphosphine) palladium(0) (0.03 g) was added saturated aqueous sodium hydrogen carbonate solution (3 ml) and a solution of 2-chlorophenylboronic acid (0.45 g) in ethanol (1 ml). The mixture was heated under reflux for 3.5 hours, cooled and then poured into ether (50 ml) and water (50 ml). The layers were separated and the aqueous phase extracted with a second portion of ether (50 ml). The combined organic layers were washed with water (2×50 ml), brine (50 ml) and then dried ($Na_2SO_4$) and evaporated. The residue was purified by column chromatography on silica gel (50 g) eluted with dichloromethane. After combination and evaporation of suitable fractions the residue was further purified by HPLC. Combination and processing of suitable fractions gave the title compound as a pale brown crystalline solid, m.p. 192–3° C.

NMR($CDCl_3$): 3.76 (br. s, 2H), 7.4 (m, 2H), 7.52 (m, 2H), 7.8 (s, 2H). MS (thermospray): M/Z [M+H] 431.2; $C_{17}H_8Cl_3F_3N_4$+H requires 430.98.

Example A22

5-Amino-3-cyano-1-(2,6-dichloro-4-trifluoromethylphenyl)-4-(1-naphthyl)pyrazole

To a rapidly stirred solution of 5-amino-3-cyano-1-(2,6-dichloro-4-trifluoromethylphenyl)-4-iodopyrazole (0.447 g) in toluene (2 ml) containing tetrakis(triphenylphosphine) palladium(0) (0.02 g) was added saturated aqueous sodium hydrogen carbonate solution (1 ml) and a solution of 1-naphthylboronic acid (0.344 g) in ethanol (1 ml). The mixture was heated under reflux for 3 hours, then left at room temperature overnight. Saturated aqueous sodium hydrogen carbonate solution (0.5 ml) and tetrakis(triphenylphosphine)palladium(0) (0.01 g) were added and the mixture heated under reflux for 3 hours. The cooled reaction mixture was then poured into ether (25 ml) and water (25 ml). The layers were separated and the aqueous phase extracted with a second portion of ether (25 ml). The combined organic layers were washed with water (2×25 ml), brine (25 ml) and then dried ($MgSO_4$) and evaporated. The residue was purified by colurn chromatography on silica gel (50 g) eluted with dichloromethane. Combination and evaporation of suitable fractions gave the title compound as an off-white crystalline solid, m.p. 208° C.

NMR($CDCl_3$): 3.65 (br. s, 2H), 7.6 (m, 4H), 7.75 (m, 1H), 7.85 (m, 2H), 7.97 (m, 2H). MS (thermospray): M/Z [M+H] 447.0; $C_{21}H_{11}Cl_2F_3N_4$+H requires 447.04.

Example A23

5-Amino-3-cyano-1-(2,6-dichloro-4-trifluoromethylphenyl)-4-(3-pyridyl)pyrazole

To a rapidly stirred solution of 5-amino-3-cyano-1-(2,6-dichloro-4-trifluoromethylphenyl)-4-iodopyrazole (0.25 g) in toluene (2 ml) containing tetrak-is(triphenylphosphine) palladium(0) (0.02 g) was added saturated aqueous sodium hydrogen carbonate solution (1 ml) and a solution of 3-pyridylboronic acid (0.153 g) in ethanol (1 ml). The mixture was heated under reflux for 5 hours, then left at room temperature ovemight and then poured into ether (25 ml) and water (25 ml). The organic layer was separated, dried (MgSO$_4$) and evaporated. The residue was taken up the minimum amount of ethyl acetate and purified by column chromatography on silica gel (20 g) eluted with dichloromethane:methanol (100:1). Combination and evaporation of suitable fractions followed by recrystallisation from ether gave the title compound as an off-white solid, m.p. 265–7° C.

NMR(CDCl$_3$): 4.38 (br. s, 2H), 7.55 (m, 1H), 7.82 (s, 2H), 8.07 (d, 1H), 8.59 (m, 1H), 8.92 (s, 1H). MS (thermospray): M/Z [M+H] 398.2; C$_{16}$H$_8$Cl$_2$F$_3$N$_5$+H requires 398.01.

Example A24

5-Amino-3-cyano-1-(2,6-dichloro-4-trifluoromethylphenyl)-4-(4-pyridyl)pyrazole

To a rapidly stirred solution of 5-amino-3-cyano-1-(2,6-dichloro-4-trifluoromethylphenyl)-4-iodopyrazole (0.25 g) in toluene (2 ml) containing tetrakis(triphenylphosphine) palladium(0) (0.02 g) was added saturated aqueous sodium hydrogen carbonate solution (1 ml) and a solution of 4-pyridylboronic acid (0.153 g) in ethanol (1 ml). The mixture was heated under reflux for 12 hours, then left at room temperature overnight and then poured into ether (25 ml) and water (25 ml). The organic layer was separated, dried (MgSO$_4$) and evaporated. The residue was taken up the minimum amount of ethyl acetate and purified by chromatography on silica gel (20 g) eluted with dichloromethane:methanol (100:1). Combination and evaporation of suitable fractions followed by recrystallisation from ether/hexane/dichloromethane gave the title compound as a white solid, m.p. 266–8° C. (decomp.).

NMR(CDCl$_3$): 4.1 (br.s, 2H), 7.52 (d, 2H), 7.82 (s, 2H), 8.71 (d, 2H). MS (thermospray): M/Z [M+H] 397.9; C$_{16}$H$_8$Cl$_2$F$_3$N$_5$+H requires 398.01.

Example A25

5-Amino-3-cyano-1-(2,6-dichloro-4-trifluoromethylphenyl)-4-(2-thienyl)pyrazole

A solution of 5-amino-3-cyano-1-(2,6-dichloro-4-trifluoromethylphenyl)-4-iodopyrazole (0.45 g) in dimethoxyethane (4 ml) containing tetrakis(triphenylphosphine)palladium(0) (0.035 g) was stirred at room temperature for 30 minutes and then heated to 80° C. Thiophene-2-boronic acid (0.14 g) and aqueous sodium carbonate solution (2 ml, 1M) were added and the mixture heated under reflux for 3 hours. The cooled reaction was poured into ether and water. The organic layer was separated, dried (MgSO$_4$) and evaporated. The residue was taken up the minimum amount of dichloromethane and silica gel (10 g) added. The solvent was removed and the residue applied to a column of silica gel (75 g) which was eluted with hexane containing increasing proportions of dichloromethane. Combination and evaporation of suitable fractions gave the title compound as a white solid. A sample recrystallised form methanol had m.p. 206–7° C.

NMR(CDCl$_3$): 4.01 (br. s, 2H), 7.18 (m, 1H), 7.38 (m, 2H), 7.79 (s, 2H). MS (thermospray): M/Z [M+H] 403.2; C$_{15}$H$_7$Cl$_2$F$_3$N$_4$S+H requires 402.98.

Example A26

5-Amino-3-cyano-1-(2,6-dichloro-4-trifluoromethylphenyl)-4-(3-thienyl)pyrazole

To a rapidly stirred solution of 5-amino-3-cyano-1-(2,6-dichloro-4-trifluoromethylphenyl)-4-iodopyrazole (0.447 g) in toluene (2 ml) containing tetrakis(triphenylphosphine) palladium(0) (0.02 g) was added saturated aqueous sodium hydrogen carbonate solution (1 ml) and a solution of thiophene-3-boronic acid (0.256 g) in ethanol (1 ml). The mixture wAas heated under reflux for 3 hours, then left at room temperature overnight. Saturated aqueous sodium hydrogen carbonate solution (0.5 ml) and tetrakis (triphenylphosphine)palladium(0) (0.01 g) were added and the mixture heated under reflux for 3 hours. Thiophene-3-boronic acid (0.178 g) and tetrakis(triphenylphosphine) palladium(0) (0.02 g) were added and heating under reflux continued for 16 hours. The cooled reaction mixture wvas then poured into ether (25 ml) and water (25 ml). The layers ere separated and the aqueous phase extracted with a second portion of ether (25 ml). The combined organic layers were washed with water (2×25 ml), brine (25 ml) and then dried (MgSO$_4$) and evaporated. The residue was purified by column chromatography on silica gel (50 g) eluted with dichloromethane. Combination and evaporation of suitable fractions gave the title compound as a white crystalline solid, m.p. 210–2° C.

NMR(CDCl$_3$): 3.9 (br. s, 2H), 7.41 (m, 1H), 7.5 (m, 2H), 7.81 (s, 2H). MS (thermospray): M/Z [M+H] 403.3; C$_{15}$H$_7$Cl$_2$F$_3$N$_4$S+H requires 402.98.

Example A27

5-Amino-3-cyano-1-(2,6-dichloro-4-triluoromethylphenyl)-4-(2-furanyl)pyrazole

A solution of 5-amino-3-cyano-1-(2,6-dichloro-4-trifluoromethylphenyl)-4-iodopyrazole (0.45 g) in dimethoxyethane (4 ml) containing tetrakis (triphenylphosphine)palladium(0) (0.035 g) was stirred at room temperature for 30 minutes and then heated to 80° C. Furan-2-boronic acid (0.125 g) and aqueous sodium carbonate solution (2 ml, 1M) were added and the mixture heated under reflux for 3 hours. The cooled reaction was poured into ether and water. The organic layer was separated, dried (MgSO$_4$) and evaporated. The residue was taken up the minimum amount of dichloromethane and silica gel (10 g) added. The solvent was removed and the residue applied to a column of silica gel (75 g) which was eluted with hexane containing increasing proportions of dichloromethane. Combination and evaporation of suitable fractions gave the title compound as an very light pink crystalline solid 195–6° C.

NMR(CDCl$_3$): 4.46 (br. s, 2H), 6.52 (d, 1H), 6.78 (d, 1H), 7.43 (s, 1H), 7.86 (s, 2H). MS (thermospray): M/Z [M+H] 387.1; C$_{15}$H$_7$Cl$_2$F$_3$N$_4$O+H requires 387.0.

Example A28

5-Amino-3-cyano-1-(2,6-dichloro-4-trifluoromethylphenyl)-4-(3-furanyl)pyrazole

To a rapidly stirred solution of 5-amino-3-cyano-1-(2,6-dichloro-4-trifluoromethylphenyl)-4-iodopyrazole (0.447 g) in toluene (2 ml) containing tetrakis(triphenylphosphine) palladium(0) (0.02 g) was added saturated aqueous sodium hydrogen carbonate solution (1 ml) and a solution of furan-3-boronic acid (0.23 g) in ethanol (1 ml). The mixture was heated under reflux for 5.5 hours, cooled and then poured into ether (25 ml) and water (25 ml). The layers were separated and the aqueous phase extracted with a second portion of ether (25 ml). The combined organic layers were washed with water (2×25 ml), brine (25 ml) and then dried (MgSO$_4$) and evaporated. The residue was purified by column chromatography on silica gel (30 g) eluted with dichloromethane. After combination and evaporation of suitable fractions the residue was further purified by HPLC. Combination and processing of suitable fractions gave the title compound as a white solid, m.p. 180–1° C.

NMR(CDCl$_3$): 3.79 (br. s, 2H), 6.79 (s, 1H), 7.6 (m, 1H), 7.78 (m, 1H), 7.82 (s, 2H). MS (thermospray): M/Z [M+H] 386.9; C$_{15}$H$_7$Cl$_2$F$_3$N$_4$O+H requires 387.0.

Example A29

5-Amino-3-cyano-1-(2,6-dichloro-4-methylphenyl)-4-(2-furanyl)pyrazole

To a stirred solution of 5-amino-3-cyano-1-(2,6-dichloro-4-methylphenyl)pyrazole (1 g) in acetonitrile (15 ml) at room temperature was added N-iodosuccinimide (0.845 g). Stirring was continued for 10 minutes and the mixture was then evaporated to dryness. The residue was taken up in dioxane (20 ml). Furan-2-boronic acid (0.845 g), tetrakis (triphenylphosphine)palladium(0) (0.35 g) and a solution of potassium carbonate (2.8 g) in water (8 ml) were added. The mixture was heated under reflux for 24 hours, then cooled and partitioned between ether and water. The separated aqueous layer was extracted with ether and the combined ether layers were washed with brine, dried and evaporated. The green oily residue was purified by column chromatography on silica gel eluted with hexane:dichloromethane (1:2). Combination and evaporation of suitable fractions followed by recrystallisation from toluene gave the title compound as a white solid, m.p. 191.5–192.5° C.

NMR(CDCl$_3$): 2.43 (s, 3H), 4.43 (br. s, 2H). 6.53 (m, 1H), 6.79 (m, 1H), 7.32 (s, 2H), 7.47 (s, 1H). Microanalysis; Found C, 53.79; H, 2.87; N, 16.65%; C$_{15}$H$_{10}$Cl$_2$F$_3$N$_4$O requires C, 54.07; H, 3.03; N, 16.82%.

Example A30

5-Amino-3-cyano-1-(2,6-dichlorophenyl)-4-(2-furanyl)pyrazole

To a stirred solution of 5-amino-3-cyano-1-(2,6-dichlorophenyl)pyrazole (0.1318 g) in acetonitrile (5 ml) at room temperature was added N-iodosuccinimide (0.1469 g). Stirring was continued for 1 hour and the mixture was then evaporated to dryness. The residue was taken up in dioxane (5 ml). Furan-2-boronic acid (0.1232 g), tetrakis (triphenylphosphine)palladium(0) (0.0554 g) and a solution of potassium carbonate (0.4405 g) in water (2 ml) were added. The mixture was heated under reflux for 48 hours, then cooled and partitioned between ether and water. The separated aqueous layer was extracted with ether and the combined ether layers were washed with brine, dried and evaporated. The green oily residue was purified by column chromatography on silica gel (4 g) eluted with dichloromethane. Combination and evaporation of suitable fractions followed by recrystallisation from toluene gave the title compound as a light brown solid, m.p. 222.6° C.

NMR(CDCl$_3$): 4.42 (br. s, 2H), 6.52 (m, 1H), 6.78 (m, 1H), 7.5 (m, 4H). MS (thermospray): M/Z [M+H] 318.8; C$_{14}$H$_8$Cl$_2$N$_4$O+H requires 319.01.

Example A31

5-Amino-4-(2-n-butylphenyl)-3-cyano-1-(2,6-dichlorophenyl-4-trifluoromethylphenyl)pyrazole To a solution of 5-amino-3-cyano-1-(2,6-dichloro-4-trifluoromethylphenyl)-4-iodopyrazole (0.367 g) in dioxan (5 ml) containing tetrakis(triphenylphosphine)palladium(0) (0.033 g) were added 2,4,6-tri(2-n-butylphenyl)boroxin (0.3 g) and a solution of potassium carbonate (0.519 g) in water (1.5 ml). The mixture was stirred and heated under reflux for 2 hours and then allowed to stand at room temperature overnight. After stirring and heating under reflux for a further 2 hours the reaction mixture was cooled and then poured into ether and dilute aqueous hydrochloric acid. The aqueous phase was separated and extracted with ether. The combined ether extracts were washed with brine, dried (Na$_2$SO$_4$) and evaporated. The residue was purified by column chromatography on silica gel eluted with hexane dichloromethane (3:1 changing to 1:1). Combination and evaporation of suitable fractions followed by recrystallisation from cyclohexane gave the title compound as a white solid, m.p. 117.1–117.7° C.

NMR(CDCl$_3$): 0.87 (t, 3H), 1.25 (m, 2H), 1.46 (m, 2H), 2.6 (m, 2H), 3.6 (br. s, 2H), 7.39 (m, 2H), 7.47 (m, 2H), 7.81 (s, 2H). MS (thermospray): M/Z [M+H] 453.0; C$_{21}$H$_{17}$Cl$_2$F$_3$N$_4$+H requires 453.09.

Example A32

5-Amino-3-cyano-4-(2,3-dichlorophenyl)-1-(2,6-dichlorophenyl-4-trifluoromethylphenyl)pyrazole To a stirred solution of 5-amino-3-cyano-1-(2,6-dichlorophenyl-4-trifluoromethyl)pyrazole (0.642 g) in acetonitrile (10 ml) at room temperature was added N-iodosuccinimide (0.46 g). Stirring was continued for 5 minutes and the mixture was then evaporated to dryness. The residue was taken up in ethanol (2 ml), toluene (4 ml) and saturated aqueous sodium hydrogen carbonate solution (20 ml). After the addition of 2,3-dichlorophenylboronic acid (0.764 g) and tetrakis(triphenylphosphine)palladium(0) (0.025 g) the mixture was stirred and heated under reflux for 24 hours. Tetrakis(triphenylphosphine)palladium(0) (0.025 g) was added and the mixture was stirred and heated under reflux for 2 hours. Saturated aqueous sodium hydrogen carbonate solution (1 ml), 2,3-dichlorophenylboronic acid (0.5 g) and tetrakis(triphenylphosphine)palladium(0) (0.025 g) were added and the mixture was stirred and heated under reflux for 24 hours. After cooling the mixture was evaporated and the residue partitioned between ether and water. The ether layer was separated, dried and evaporated. The residue was purified by column chromatography on silica gel (50 g) eluted with hexane/dichloromethane mixtures. Combination and evaporation of suitable fractions followed by recrystallisation from isopropanol gave the title compound as a white solid, m.p. 201–202° C.

NMR(CDCl$_3$): 3.79 (br. s, 2H), 7.38 (dd, 1H), 7.44 (d, 1H), 7.58 (d, 1H), 7.82 (s, 2H). Microanalysis: Found C, 43.66; H, 1.51; N, 11.97%; C$_{17}$H$_7$Cl$_4$F$_3$N$_4$ requires C, 43.81; H, 1.51; N, 12.02%.

Preparation B1

5-Amino-3-cyano-1-(2,6-dichloro-4-trifluoromethylphenyl)-4-trimethylsilylethynylpyrazole To a stirred solution of 5-amino-3-cyano-1-(2,6-dichloro-4-trifluoromethylphenyl)-4-iodopyrazole (6.96 g, crude from Preparation A1) in triethylamine (30 ml) and dimethylformnamide (6 ml) at room temperature was added trimethylsilylacetylene (3 ml), cuprous iodide (150 mg) and bis(triphenylphosphine)palladium(II) chloride (300 mg). The mixture was heated at 50–60° C. for one hour, trimethylsilylacetylene (0.3 ml) was then added and stirring and heating continued for a further period of 30 minutes. The cooled reaction mixture was diluted with water (250 ml) extracted with ether (250 ml). The organic layer was separated (aided by the addition of brine). The aqueous layer was re-extracted with ether (250 ml). The combined ether extracts were dried ($MgSO_4$) and evaporated to give the crude product as a gum (4.67 g).

Purification by column chromatography on silica gel eluted with dichloromethane:hexane (1:1) followed by recrystallisation from ether/hexane provided the title compound as a white solid m.p. 181–2° C.

NMR($CDCl_3$): 0.2 (s, 9H), 4.1 (br. s, 2H), 7.7 (s, 2H). MS (thermospray): M/Z [M+$NH_4$]434.2; $C_{16}H_{13}Cl_2F_3N_4Si$+$NH_4$ requires 434.0

Preparation B2

5-Amino-3-cyano-1-(2,6-dichloro-4-trifluoromethylphenyl)-4-ethynylpyrazole

To a stirred solution of 5-amino-3-cyano-1-(2,6-dichloro4-trifluoromethylphenyl)-4-trimethylsilylethynylpyrazole (2.0 g, crude from example B1) in methanol (30 ml) was added potassium carbonate (1 g). After 10 minutes at room temperature the reaction mixture was partitioned between ether (100 ml) and water (100 ml). The organic layer was separated, washed with brine (100 ml), dried ($MgSO_4$) and evaporated. The residue was purified by column chromatography on silica gel eluted with dichloromethane folloxwed by recrystallisation from ether to provide the title compound as a white solid m.p. 215–216° C.

NMR($CDCl_3$): 3.49 (s, 1H), 4.2 (br. s, 2H), 7.8 (s, 2H) MS (thermospray): M/Z [M+$NH_4$] 362.4; $C_{13}H_5Cl_2F_3N_4$+$NH_4$ requires 362.0

Example B3

5-Amino-4-(3-bromoisoxazol-5-yl)-3-cyano-1-(2,6-dichloro-4-trifluoromethylphenyl)pyrazole To a rapidly stirred mixture of 5-amino-3-cyano-1-(2,6-dichloro-4-trifluoromethylphenyl-4-ethynylpyrazole (0.2 g) in ethyl acetate (5 ml) and potassium hydrogen carbonate (0.11 g) in water (0.75 ml) at room temperature was added, portionwise, dibromoformaldoxime (0.13 g). After 20 hours dibromoformaldoxime (0.13 g) was added and stirring continued for a further 24 hours. The reaction mixture was evaporated to approximately 10% of its original volume and the partitioned between water (25 ml) and dichloromethane (25 ml). The organic layer was separated, washed with water (25 ml), dried ($Na_2SO_4$) and evaporated. The residue was purified by column chromatography on silica gel eluted with dichloromethane. Combination and evaporation of suitable fractions gave the title compound as a white crystalline solid, m.p. 227° C.

NMR($CDCl_3$): 4.86 (br. s, 2H), 6.78 (s, 1H), 7.83 (s, 2H). MS (thermospray): M/Z [M+$NH_4$] 482.8; $C_{14}H_5Br3Cl_2F_3N_5O$+$NH_4$ requires 482.94.

Preparation B4

3-Cyano-1-(2,6-dichloro-4-trifluoromethylphenyl)-4-iodopyrazole

To a stirred solution of 5-amino-3-cyano-1-(2,6-dichloro-4-trifluoromethylphenyl)-4-iodopyrazole (90 g) in tetrahydrofuran (720 ml) heated to 65° C. was added t-butylnitrite (144 ml) over a period of 0.5 hours. Stirring and heating were continued for 3 hours. The cooled reaction mixture was evaporated and the residue recrystallised from propan-2-ol to give the title compound as a white solid, m.p.83–4° C.

NMR($CDCl_3$): 7.7 (s, 1H), 7.79 (s, 2H). MS (thermospray,): M/Z [M+$NH_4$] 448.8; $C_{11}H_3Cl_2F_3N_3I$+$NH_4$ requires 448.9.

Preparation B5

3-Cyano-1-(2,6-dichloro-4-trifluoromethylpbenyl)-4-ethenylpyrazole

A solution of 3-cyano-1-(2,6-dichloro-4-trifluoromethylphenyl)-4-iodopyrazole (58 g) in dimethylformamide (350 ml) containing vinyltri-n-butyltin (1 16 ml) and tetrakis(triphenylphosphine)palladium(0) (3.5 g) was stirred at 75° C. for 3 hours. The reaction mixture was poured into water (600 ml) and ether (600 ml). The organic layer was separated, washed with water (x5), brine (700 ml), dried ($Na_2SO_4$) and evaporated. The residue was recrystallised from propan-2-ol to give the title compound as a pale brown solid, m.p.75–6° C.

NMR($CDCl_3$): 5.5 (d, 1H), 5.94 (d, 1H), 6.64 (dd, 1H), 7.64 (s, 1H), 7.77 (s, 2H). MS (thermospray): M/Z [M+$NH_4$] 349.5; $C_{13}H_6Cl_2F_3N_3$+$NH_4$ requires 349.02.

Preparation B6

3-Cyano-1-(2,6-dichloro-4-trifluoromethylphenyl)-4-formylpyrazole

A solution of 3-cyano-1-(2,6-dichloro-4-trifluoromethylphenyl)-4-ethenylpyrazole (0.1 g), N-methylmorpholine oxide (0.005 g), osmium tetroxide (5011 of a 2.5% solution in t-butanol) in water (5 ml) and acetone (45 ml) was stirred at room temperature for 16 hours Sodium metaperiodate (0.005 g) was added and stirring continued for 16 hours. The reaction mixture was evaporated and the residue partititoned between ether and aqueous sodium hydrogen carbonate solution. The aqueous layer was separated and extracted with ether. The combined ether extracts were dried ($Na_2SO_4$) and evaporated. The residue was purified by column chromatography on silica gel (5 g) eluted with dichloromethane. Combination and evaporation of suitable fractions gave the title compound as a biege solid, m.p. 167.5–168.5° C.

NMR($CDCl_3$): 7.8 (s, 2H), 8.18 (s, 1H), 10.08 (s, 1H). MS (thermospray): M/Z [M+$NH_4$] 351.3; $C_{12}H_4Cl_2F_3N_3O$+$NH_4$ requires 351.0.

Preparation B7

3-Cyano-1-(2,6-dichloro-4-trifluoromethylphenyl)-4-(4,4-diethoxy-1-hydroxybut-2-ynyl)pyrazole To a solution of propionaldehyde diethyl acetal (0.0192 g) in anhydrous tetrahydrofuran (2 ml) cooled to −78° C. under an atmosphere of nitrogen was added dropwise n-butyl lithium (621 μl, 2.5M in hexanes) and the mixture was stirred for 10 minutes. 3-Cyano-1-(2,6-dichloro-4-trifluoromethylphenyl)-4-formylpyrazole (0.05 g) was added and stirring continued for 30 minutes. The reaction mixture was poured into water (5 ml) and ether (5 ml). The organic layer was separated, dried ($Na_2SO_4$) and evaporated. The residue was purified by column chromatography on silica gel (5 g) eluted with dichloromethane. Combination and evaporation of suitable fractions gave the title compound as a white foam.

NMR(CDCl$_3$): 1.23 (t, 6H), 2.6 (d, 1H), 3.6 (m, 2H), 3.75 (m, 2H), 5.35 (s, 1H), 5.73 (d, 1H), 7.73 (s, 1H), 7,75 (s, 2H).

Example B8

4-(3-Bromofuran-2-yl)-3-cyano-1-(2,6-dichloro-4-trifluoromethylphenyl) pyrazole

To a stirred solution of 3-cyano-1-(2,6-dichloro-4-trifluoromethylphenyl)-4-(4,4-diethoxy-1-hydroxybut-2-ynyl)pyrazole (0.04 g) in dioxane (1 ml) was added dropwise at room temperature hydrobromic acid (0.04 g). After 30 minutes the reaction mixture was poured into water (10 ml) and ether (10 ml). The organic layer was separated, dried (MgSO$_4$) and evaporated. Recrystallisation from ether/hexane gave the title compound as a pale brown solid, m.p. 99–101° C.

NMR(CDCl$_3$): 6.6 (d, 1H), 7.55 (d, 1H), 7.79 (s, 2H), 8.3 (s, 1H). MS (thermospray): M/Z [M+NH$_4$] 466.3; C$_{15}$H$_5$BrCl$_2$F$_3$N$_4$O+NH$_4$ requires 466.92.

Preparation B9

4-Acetyl-5-amino-3-cyano-1-(2,6-dichloro-4-trifluoromethylphenyl)pyrazole

To a solution of 5-amino-3-cyano-1-(2,6-dichloro-4-trifluoromethylphenyl)-4-ethynylpyrazole (0.345 g) in acetonitrile (5 ml) was added p-toluenesulphonic acid (0.5 g) and the mixture was stirred at room temperature for 2 hours and then poured into water (100 ml) and ether (100 ml). The organic layer was separated, washed with saturated aqueous sodium hydrogen carbonate solution (50 ml), brine (50 ml), dried (Na$_2$SO$_4$) and evaporated. The residue was purified by column chromatography on silica gel (40 g) eluted with dichloromethane:hexane (10:1). Combination and evaporation of suitable fractions gave the title compound as a white crystalline solid, m.p. 200–1° C.

NMR(CDCl$_3$): 2.65 (s, 3H), 5.83 (br. s, 2H), 7.82 (s, 2H). MS (thermospray): M/Z [M+NH$_4$] 380.4; C$_{13}$H$_7$Cl$_2$F$_3$N$_4$O+NH$_4$ requires 380.03.

Preparation B10

5-Amino-4-bromoacetyl-3-cyano-1-(2,6-dichloro-4-trifluoromethylphenyl)pyrazole

A solution of 4-acetyl-5-amino-3-cyano-1-(2,6-dichloro-4-trifluoromethylphenyl)pyrazole (0.5 g) in dioxane (10 ml) containg cupric bromide (0.612 g) was heated under reflux for 4 hours then left at room temperature for 48 hours. Cupric bromide (0.2 g) was added and the mixture was heated under reflux for 3 hours then left at room temperature for 24 hours. The reaction mixture was poured into water (50 ml) and ether (50 ml). The organic layer was separated, filtered, dried (MgSO$_4$) and evaporated. The residue was purified by column chromatography on silica gel eluted with dichloromethane. Combination and evaporation of suitable fractions gave the title compound as a white solid, m.p. 190–2° C.

NMR(CDCl$_3$): 4.49 (s, 2H), 5.93 (br. s, 2H), 7.82 (s, 2H).

Example B11

5-Amino-3-cyano-1-(2,6-dichloro-4-trifluoromethylphenyl)-4-(2-methylthiazol-4-yl)pyrazole To a solution of 5-amino-4-bromoacetyl-3-cyano-1-(2,6-dichloro-4-trifluoromethylphenyl)pyrazole (0.1 g) in ethanol (5 ml) was added thioacetamide (0.0375 g). After 1 hour at room temperature the mixture was evaporated and the residue was purified by column chromatography on silica gel (10 g) eluted with dichloromethane. Combination and evaporation of suitable fractions gave the title compound as a white solid, m.p. 226–8° C.

NMR(d$_6$-dmso): 2.72 (s, 3H), 6.6 (br. s, 2H), 7.53 (s, 1H), 7.8 (s, 2H). MS (thermospray): M/Z [M+H] 418.2; C$_{15}$H$_8$Cl$_2$F$_3$N$_5$S+H requires 417.99.

Example C1

5-Amino-4-(5-bromothien-2-yl)-3-cyano-1-(2,6-dichloro-4-trifluoromethylphenyl)pyrazole To a solution of 5-amino-3-cyano-1-(2,6-dichloro-4-trifluoromethylphenyl)-4-(thien-2-yl)pyrazole (0.153 g) in acetonitrile (12 ml) was added N-bromosuccinimide (0.068 g). The mixture was left at room temperature for 1.5 hours and then poured into ether (50 ml) and water (50 ml). The layers were separated and the aqueous phase extracted with a second portion of ether (50 ml). The combined organic layers were washed with water (25 ml), then dried (MgSO$_4$) and evaporated. The residue was purified by column chromatography on silica gel (10 g) eluted with dichloromethane. Combination and evaporation of suitable fractions gave the title compound as an off-white solid, m.p. 214° C.

NMR(CDCl$_3$): 3.99 (br. s, 2H), 7.1 (m, 2H), 7.8 (s, 2H) MS (thermospray): M/Z [M+NH$_4$] 498.0; C$_{15}$H$_6$BrCl$_2$F$_3$N$_4$S+NH$_.$; requires 497.92.

Example C2

5-Amino-3-cyano-1-(2,6-dicbloro-4-trifluoromethylphenyl)-4-(5-trifluoromethylsulphenylthien-2-yl)pyrazole To a stirred solution of 5-amino-3-cyano-1-(2,6-dichloro-4-trifluoromethylphenyl)-4-(thien-2-yl)pyrazole (0.806 g) in dry dichloromethane (25 ml) at room temperature was added a solution of stannic chloride (500 µl) in dry dichloromethane (5 ml). To this was added 7.2 ml of a 50 mg/ml solution of trifluoromethylsulphenyl chloride in dichloromethane and the mixture was stirred for 48 hours after which it was poured onto a mixture of ice, water and dichloromethane. The aqueous layer was separated and washed with dichloromethane. The combined organic layers were washed with saturated aqueous sodium hydrogen carbonate solution, dried and evaporated. The residue was purified by column chromatography on silica gel (40 g) eluted with dichloromethane:hexane (1:1). Combination and evaporation of suitable fractions gave the title compound as a white solid, m.p. 162–3° C.

NMR(CDCl$_3$): 4.12 (br. s, 2H), 7.39 (d, 1H), 7.46 (d, 1H), 7.8 (s, 2H) MS (thermospray): M/Z [M+H] 502.9; C$_{16}$H$_6$Cl$_2$F$_6$N$_4$S$_2$+H requires 502.94.

Example C3

5-Amino-3-cyano-4-(3,4-dibromoisoxazol-5-yl)-1-(2,6-dichloro-4-trifluoromethylphenyl)pyrazole To a solution of 5-amino-4-(3-bromoisoxazol-5-yl)-3-cyano-1-(2,6-dichloro-4-trifluoromethylphenyl)pyrazole (0.05 g) in acetonitrile (6 ml) was added N-bromosuccinimide (0.02 g). The mixture was left at room temperature for 24 hours during which time a precipitate formed which was isolated by filtration. Washing with methanol, followed by drying, afforded the title compound as a white solid, m.p. 279° C.

NMR(CDCl$_3$): 4.49 (br. s, 2H), 7.82 (s, 2H) MS (thermospray): M/Z [M+NH$_4$] 561.0; C$_{14}$H$_4$Br$_2$Cl$_2$F$_3$N$_5$O+NH$_4$ requires 560.85.

Example C4

5-Amino-4-(2-chlorofuran-3-yl)-3-cyano-1-(2,6-dichloro-4-trifluoromethylpbenyl)pyrazole To a solution of 5-amino-3-cyano-1-(2,6-dichloro-4-trifluoromethylphenyl)-4-(furan-3-yl)pyrazole (0.095 g) in acetonitrile (6 ml) was added N-chlorosuccinimide (0.0345 g). The mixture was left at room temperature for 1.5 hours and then poured into ether (50 ml) and water (50 ml). The layers were separated and the aqueous phase extracted with a second portion of ether (50 ml). The combined organic layers were washed with water (25 ml), then dried (Na$_2$SO$_4$) and evaporated. The residue was purified by column chromatography on silica gel (10 g) eluted with dichloromethane. Combination and evaporation of suitable fractions gave the title compound as a white solid, m.p. 153° C.

NMR(CDCl$_3$): 4.86 (br. s, 2H), 6.73 (d, 1H), 7.49 (d, 1H), 7.82 (s, 2H) MS (thermospray): M/Z [M+H] 421.0; C$_{15}$H$_6$Cl$_3$F$_3$N$_4$O+H requires 420.96.

Example C5

5-Amino-4-(2-bromofuran-3-yl)-3-cyano-1-(2,6-dichloro-4-trifluoromethylphenyl)pyrazole To a solution of 5-amino-3-cyrano-1-(2,6-dichloro-4-trifluoromethylphenyl)-4-(furan-3-yl)pyrazole (0.600 g) in tetrahydrofuran (20 ml) was added N-bromosuccinimide (0.288 g). The mixture was left at room temperature for 2 hours and then poured onto a column of silica gel (30 g) and eluted with hexane dichloromethane (1:1). Combination and evaporation of suitable fractions gave a red oil which was further purified by column chromatography on silica gel (30 g) eluted with hexane:dichloromethane (1:1), then dichloromethane. Combination and evaporation of suitable fractions gave the title compound as a white solid.

NMR(d$_6$-dmso): 6.18 (br. s, 2H), 6.74 (d, 1H), 7.93 (d, 1H), 8.26 (s, 2H) MS (thermospray): M/Z [M+H] 464.3; C$_{15}$H$_6$BrCl$_2$F$_3$N$_4$O+H requires 464.91.

Example C6

5-Amino-3-cyano-1-(2,6-dichloro-4-trifluoromethylpbenyl)-4-(2-trifluoromethylthiofuran-3-yl)pyrazole To a solution of 5-amino-3-cyano-1-(2,6-dichloro-4-trifluoromethylphenyl)-4-(furan-3-yl)pyrazole (0.310 g) in dichloromethane (10 ml) stirred at 0° C. was added dropwise trifluoromethylsulphenylchloride in dichloromethane (2.04 ml of a 66.5 mg/ml solution). The mixture allowed to warm to room temperature, and stirred for 16 hours. The reaction mixture was washed with saturated aqueous sodium hydrogen carbonate solution (25 ml). The organic layer was separated, dried (Na$_2$SO$_4$), and evaporated. The residue as purified by column chromatography on silica gel (5 g) eluted with hexane:dichloromethane (1:1), then dichloromethane. Combination and evaporation of suitable fractions gave the title compound as a white solid, m.p.162° C.

NMR(CDCl3): 3.96 (br. s, 2H), 6.85 (d, 1H), 7.82 (d, 1H), 7.82 (s, 2H) MS (themospray): M/Z [M+NH$_4$] 503.6; C$_{16}$H$_6$Cl$_2$F$_6$N$_4$OS+NH$_4$ requires 503.98.

Example C7

5-Amino-3-cyano-1-(2,6-dichloro-4-trifluoromethylphenyl)-4-(2-trifluoromethylsulphinylfuran-3-yl)pyrazole To a stirred solution of 5-amino-3-cyano-1-(2,6-dichloro-4-trifluoromethylphenyl)-4-(2-trifluoromethylthiofuran-3-yl)pyrazole (0.1 g) in dichloromethane (6 ml) stirred at −78° C. was added m-chloroperbenzoic acid (0.2 g) and the mixture allowed to warm to room temperature over a period of 1 hour. m-Chloroperbenzoic acid (0.15 g) was added and stirring was continued overnight. Dimethylsulphide (0.02 ml) was added and the reaction mixture was partitioned between saturated aqueous sodium hydrogen carbonate solution (75 ml) and dichloromethane (25 ml). The organic layer was separated, washed with water (25 ml), dried (Na$_2$SO$_4$) and evaporated. The residue was purified by column chromatography on silica gel (5 g) eluted with hexane:dichloromethane (8:1). Combination and evaporation of suitable fractions, followed by trituration with hexane, gave the title compound as a white solid, m.p. 141–142° C.

NMR(CDCl3): 5.64 (br. s, 2H), 6.65 (d, 1H), 7.8 (d, 1H), 7.82 (s, 2H) MS (thermospray): M/Z [M+H] 502.8; C$_{16}$H$_6$Cl$_2$F$_6$N$_4$O$_2$S+H requires 502.96.

Example C8a and C8b

5-Amino-3-cyano-1-(2,6-dichloro-4-trifluoromethylphenyl)-4-(2-trifluoromethylfuran-3-yl)pyrazole and 5-amino-3-cyano-1-(2,6-dichloro-4-trifluoromethylpbenyl)-4-(5-trifluoromethylfuran-3-yl)pyrazole To a solution of 5-amino-3-cyano-1-(2,6-dichloro-4-trifluoromethylphenyl)-4-(furan-3-yl)pyrazole (0.5 g) in dimethylformamide (15 m) and water (5 ml) was added sodium dithionite (0.112 g) and disodium hydrogen phosphate (0.067 g). The mixture placed in a 400 ml Parr vessel, which was evacuated, then charged with trifluoromethylbromide gas to 20 psi. The mixture was shaken and heated at 50° C., for 2.5 hours, then left at room temperature for 16 hours. The vessel Mwas then evacuated, then charged with trifluoromethylbromide to 40 psi, then shaken and heated to 50° C. for a further 7 hours, then left at room temperature for 16 hours. Further sodium dithionite (0.120 g) and disodium hydrogen phosphate (0.080 g) was added, the vessel evacuated, then charged with trifluoromethylbromide to 40 psi, then shaken and heated to 50° C. as before for 9 hours, then left at room temperature for 48 hours. Further sodium dithionite (0.240 g) and disodium hydrogen phosphate (0.160 g) were added, the vessel was evacuated, then charged w-ith trifluoromethylbromide to 45 psi, then shaken and heated to 50° C. as before for a further 9 hours. The mixture was filtered and then poured into ether (100 ml) and water (100 ml). The organic layer was separated, washed twice with water (50 ml), dried (Na$_2$SO$_4$), and evaporated. The residue was purified by column chromatography on silica gel (25 g) eluted with dichloromethane. Combination and evaporation of suitable fractions gave 5-amino-3-cyano-1-(2,6-dichloro-4-trifluoromethylphenyl)-4-(2-trifluoromethylfuran-3-yl)pyrazole as a white solid, m.p. 155–7° C.

NMR(CDCl$_3$): 3.79 (br. s, 2H), 6.70 (d, 1H), 7.70 (d, 1H), 7.82 (s, 2H) MS (thermospray): M/Z [M+H] 454.8; C$_{16}$H$_6$Cl$_2$F$_6$N$_4$O+H requires 455.0.

The residue obtained by evaporation of fractions containing longer retained materials was further purified by reverse phase high performance liquid chromatography to give 5-amino-3-cyano-1-(2,6-dichloro-4-trifluoromethylphenyl)-4-(5-tri fluoromethylfuran-3-yl)pyrazole as an amorphous pale brown solid.

NMR($d_6$-dmso): 6.55 (q, 1H), 6.64 (s, 1H), 7.1 (br. s, 2H), 8.28 (s, 2H) MS (thermospray): M/Z [M+H] 471.0; $C_{16}H_6Cl_2F_6N_4O$+H requires 472.02.

Example C9

5-Amino-3-cyano-1-(2,6-dichloro-4-trifluoromethylphenyl)-4-(5-trifluoromethylfuran-2-yl)pyrazole To a solution of 5-amino-3-cyano-1-(2,6-dichloro-4-trifluoromethylphenyl)-4-(furan-2-yl)pyrazole (0.46 g) in dimethylformamide (15 ml) and water (5 ml) was added sodium dithionite (0.286 g) and disodium hydrogen phosphate (0.17 g). The mixture placed in a 400 ml Parr vessel, which was evacuated, then charged with trifluoromethylbromide gas to 40 psi. The mixture was shaken and heated at 45° C., for 3 hours, then left at room temperature for 16 hours. The vessel was then evacuated, then recharged with trifluoromethylbromide to 40 psi, then shaken and heated to 45° C. for a further 9 hours, then left at room temperature for 48 hours. The vessel was then evacuated, then recharged with trifluoromethylbromide to 40 psi, then shaken and heated to 45° C. for a further 7 hours, then left at room temperature for 16 hours. The mixture was filtered and then poured into brine (25 ml) and extracted with ether (25 ml, ×3). The combined organic layers were washed with water (20 ml), dried ($Na_2SO_4$), and evaporated. The residue was purified by column chromatography on silica gel (25 g) eluted with hexane:ether (50:50 changing gradually to 20:80). Combination and evaporation of suitable fractions gave the title compound as a pale yellow solid, m.p. 148–151° C.

NMR($CDCl_3$): 3.53 (br. s, 2H), 6.87 (d, 1H), 6.96 (d, 1H), 7.82 (s, 2H) MS (thermospray): M/Z [M+H] 455.1; $C_{16}H_6Cl_2F_6N_4O$+H requires 455.0.

Example C10

5-Amino-3-cyano-4-(2,5-dichlorofuran-3-yl)-1-(2,6-dichloro-4-trifluoromethylphenyl)pyrazole To a solution of 5-amino-4-(2-chlorofuran-3-yl)-3-cyano-1-(2,6-dichloro-4-trifluoromethylphenyl)pyrazole (0.15 g) in tetrahydrofuran (7 ml) was added N-chlorosuccinimide (0.048 g). The mixture was left at room temperature for 24 hours and then heated at 50° C. for 3 hours and then left at room temperature for 96 hours. The reaction mixture was poured into ether (25 ml) and water (25 ml). The organic layer was washed with water (25 ml), then dried ($Na_2SO_4$) and evaporated. The residue was purified by column chromatography on silica gel (10 g) eluted with hexane:dichloromethane (50:50). Combination and evaporation of suitable fractions gave the title compound as a white solid, m.p. 193–194° C.

NMR($CDCl_3$): 3.9 (br. s, 2H), 6.52 (d, 1H), 7.8 (s, 2H) MS (thermospray): M/Z [M+H] 454.7; $C_{15}H_5Cl_4F_3N_4O$+H requires 454.

Example C11

4-(2-Bromofuran-3-yl)-3-cyano-1-(2,6-dichloro-4-trifluoromethyl-phenyl)pyrazole

To a stirred solution of 3-cyano-1-(2,6-dichloro-4-trifluoromethylphenyl)-4-(furan-3-yl)pyrazole (0.19 g) in tetrahydrofuran (5 ml) was added portionwise N-bromosuccinimide (0.093 g). The mixture was left at room temperature for 24 hours and then poured into ether (15 ml) and water (15 ml). The layers were separated and the organic layer was dried ($Na_2SO_4$) and evaporated. The residue was purified by column chromatography on silica gel (10 g) eluted with hexane:dichloromethane (1:1). Combination and evaporation of suitable fractions gave the title compound as a white solid, m.p. 111° C.

NMR($CDCl_3$): 7.1 (d, 1H), 7.6 (d, 1H), 7.8 (s, 2H), 8.13 (s, 1H) MS (thermospray): M/Z [M+H] 450.4; $C_{15}H_5BrCl_2F_3N_3O$+H requires 449.9.

Example D1

3-Cyano-1-(2,6-dichloro-4-trifluoromethylphenyl)-4-(2-trifluoromethylphenyl)pyrazole To a solution of 5-amino-3-cyano-1-(2,6-dichloro-4-trifluoromethylphenyl)-4-(2-trifluoromethylphenyl)pyrazole (0.114 g) in tetrahydrofuran (2.5 ml) was added t-butyl nitrite (87 μl). The mixture was heated to 65° C. for 1 hour, then cooled and evaporated. The residue was taken up in t-butanol and freeze dried to give the title compound as a pale brown solid, m.p. 142–3° C.

NMR($CDCl_3$): 7.63 (m, 2H) 7.71 (m, 1H), 7.77 (m, 1H), 7.82 (s, 2H), 7.86 (m, 1H). MS (thermospray): M/Z [M+H] 466.6; $C_{18}H_7Cl_2F_6N_3O$+H requires 465.99.

Example D2

3-Cyano-1-(2,6-dichloro-4-trifluoromethylphenyl)-4-(furan-2-yl)pyrazole

To a solution of 5-amino-3-cyano-1-(2,6-dichloro-4-trifluoromethylphenyl)-4-(furan-2-yl)pyrazole (0.081 g) in tetrahydrofuran (2 ml) was added t-butyl nitrite (74 μl). The mixture was heated to 65° C. for 1 hour, then cooled and evaporated. The residue was purified by column chromatography on silica gel (5 g) eluted with hexane containing increasing amounts of ether (up to 10%). Combination and evaporation of appropriate fraction gave the title compound as a white solid.

NMR($CDCl_3$): 6.57 (m, 1H), 6.96 (d, 1H), 7.5 (d, 1H), 7.8 (s, 2H), 7.89 (s, 1H). MS (thermospray): M/Z [M+H] 371.9; $C_{15}H_6Cl_2F_3N_3O$+H requires 371.99.

Example D3

4-(3-Bromoisoxazol-5-yl)-3-cyano-1-(2,6-dichloro-4-trifluoromethyiphenyl)pyrazole To a solution of 5-amino-4-(3-bromoisoxazol-5-yl)-3-cyano-1-(2,6-dichloro-4-trifluoromethylphenyl)pyrazole (0.1 g) in tetrahydrofuran (1.5 ml) was added t-butyl nitrite (77 μl). The mixture was heated to 65° C. for 1 hour, then cooled and evaporated. The residue was taken up in t-butanol and freeze dried to give the title compound as a pale yellow solid, m.p. 145° C.

NMR($CDCl_3$): 6.95 (s, 1H), 7.82 (s, 2H), 8.13 (s, 1H). MS (thermospray): M/Z [M+$NH_4$] 467.5; $C_{14}H_4BrCl_2F_3N_4O$+$NH_4$ requires 467.5.

Example D4

3-Cyano-1-(2,6-dichloro-4-trifluoromethylphenyl)-4-(furan-3-yl)pyrazole

To a solution of 5-amino-3-cyano-1-(2,6-dichloro-4-trifluoromethylphenyl)-4-(furan-3-yl)pyrazole (0.204 g) in tetrahydrofuran (3 ml) was added t-butyl nitrite (187.8 μl). The mixture was heated to 65° C. for 1 hour, then cooled and evaporated The residue was purified by column chromatography on silica gel (5 g) eluted with hexane containing increasing amounts of dichloromethane (up to 100%). Combination and evaporation of appropriate fraction gave the title compound as a white solid, m.p. 139° C.

NMR(CDCl$_3$): 6.7 (s 1H), 7.53 (s, 1H), 7.73 (s, 1H), 7.79 (s, 2H), 7.99 (s, 1H). MS (thermospray): M/Z [M+H] 372.0; C$_{15}$H$_6$Cl$_2$F$_3$N$_3$O+H requires 371.99.

Example D5

4-(2-Chlorofuran-3-yl)-3-cyano-1-(2,6-dichloro-4-trifluoromethylphenyl)pyrazole

To a solution of 5-amino-4-(2-chlorofuran-3-yl)-3-cyano-1-(2,6-dichloro-4-trifluoromethylphenyl)pyrazole (0.204 g) in tetrahydrofuran (3 ml) was added t-butyl nitrite (171.8 μl). The mixture was heated to 65° C. for 1 hour, then cooled and evaporated. The residue was purified by column chromatography on silica gel (10 g) eluted with hexane containing increasing amounts of dichloromethane (up to 100%). Combination and evaporation of appropriate fraction gave the title compound as a white solid, m.p. 125° C.

NMR(CDCl$_3$): 7.13 (d, 1H), 7.47 (d, 1H), 7.8 (s, 2H) 8.07 (s, 1H). MS (thermospray): M/Z [M+H] 406.0; C$_{15}$H$_5$Cl$_3$F$_3$N$_3$O+H requires 405.95.

What is claimed is:

1. A compound of the formula (I)

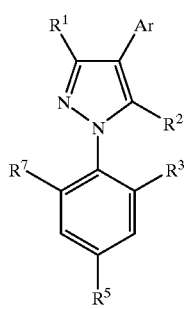

(I)

wherein

R$^1$ is CN, or CF$_3$,

R$^2$ is H or NH$_2$,

R$^3$ is halogen,

R$^5$ is H, C$_{1-6}$ alkyl optionally substituted by one or more halogen atoms, C$_{1-6}$ alkoxy optionally substituted by one or more halogen atoms or SF$_5$, R$^7$ is halogen, and Ar is phenyl, 3,4-methylenedioxyphenyl, napth-1-yl, pyridin-3-yl, pyridin-4-yl, thien-2-yl, thien-3-yl, furan-2-yl, furan-3-yl, thiazol-4-yl or isoxazol-5-yl, each optionally substituted by one or (independently) more halogen atoms, C$_{1-6}$ alkyl optionally substituted by one or more halogen atoms, C$_{1-6}$ alkoxy optionally substituted by one or more halogen atoms, C$_{1-6}$ alkoxycarbonyl optionally substituted by one or more halogen atoms, NO$_2$, NH$_2$, CN or S(O)$_m$(C$_{1-6}$alkyl optionally substituted by one or more halogen atoms), and pharmaceutically or veterinarily acceptable salts thereof.

2. A compound or salt according to claim 1 wherein R$^3$ is Cl.

3. A compound or salt according to claim 1 wherein R$^5$ is H, CH$_3$, CF$_3$, OCF$_3$ or SF$_3$.

4. A compound or salt according to claim 2 wherein R$^5$ is H, CH$_3$, CF$_3$, OCF$_3$ or SF$_5$.

5. A compound or salt according to claim 1 wherein R$^1$ is Cl.

6. A compound or salt according to claim 2 wherein R$^7$ is Cl.

7. A compound or salt according to claim 3 wherein R$^7$ is Cl.

8. A compound or salt according to claim 4 wherein R$^7$ is Cl.

9. A compound or salt according to any of claims 1 to 9, wherein Ar is 4-methylphenyl, phenyl, 2-n-butylphenyl, 3–nitrophenyl, 4-bromophenyl, 4-chlorophenyl, 4-fluorophenyl, 3,5-dichlorophenyl, 2,3-dichlorophenyl, 3-chloro-4-fluorophenyl, 3-methoxycarbonylphenyl, 3-aminophenyl, 4-methoxyphenyl, 3,4-methylenedioxyphenyl, 3,4-dimethoxyphenyl, 3-fluorophenyl, 3-chlorophenyl, 2-fluorophenyl, 2-methoxyphenyl, 2-methylphenyl, 2-trifluoromethylphenyl, 2-chlorophenyl, naphth-1-yl, pyridin-3-yl, pyridin-4-yl, thien-2-yl, thien-3-yl, furan-2-yl, furan-3-yl, 3-bromoisoxazol-5-yl, 3-bromofuran-2-yl, 5-bromothien-2-yl, 5-trifluoromethylthiothien-2-yl, 3,4-dibromoisoxazol-5-yl, 2-chlorofuran-3-yl, 2-bromofuran-3-yl, 2-methylthiazol-4-yl, 2-trifluoromethylsulphinylfuran-3-yl, 5-trifluoromethylfuran-3-yl, 5-trifluoromethylfuran2-yl, 2,5-dichlorofuran-3-yl, 3-trifluoromethylfuran-2-yl and 2-trifluoromethylfuran-3-yl.

10. A compound or salt according to any of claims 1 to 8, wherein Ar is phenyl, furan-2-yl, furan-3-yl, thien-2-yl, thien-3-yl or isoxazol-5-yl, each optionally substituted with halogen, C$_{1-6}$ alkoxy optionally substituted by one or more halogen atoms or C$_{1-6}$ alkyl optionally substituted by one or more halogen atoms or S(O)$_m$(C$_{1-6}$ alkyl optionally substituted by one or more halogen atoms) at the position adjacent to the atom which forms a bond to the 4-position of the pyrazole.

11. A compound or salt according to any of claims 1 to 8, wherein Ar is 2-fluorophenyl, 2-methylphenyl, 2-n-butylphenyl, 2,3-dichlorophenyl, 2-methylthiazol-4-yl, 2-trifluromethylsulphinylfuran-3-yl, 2,5-dichlorofuran-3-yl, 2-trifluoromethylphenyl, 2-chlorophenyl, 3-bromofuran-2-yl, 3,4-dibromoisoxazol-5-yl, 3-chlorofuran-2-yl, 2-bromofuran-3-yl, or 2-trifluoromethylfuran-3-yl.

12. A pharmaceutical or veterinary parasiticidal formulation comprising a compound of formula (I) or salt thereof according to any of claims 1 to 8, in admixture with a compatible adjuvant, diluent or carrier.

13. An agricultural formulation comprising a comprising a compound of formula (I) or salt thereof, according to any of claims 1 to 8, in admixture with a compatible adjuvant, diluent or carrier.

14. A method of treating a parasitic infestation at a locus, which comprises treating the locus with an effective amount of a compound or salt as defined in any one of claims 1 to 8, or with a formulation thereof, as defined in claim 12 or 13.

15. A method of treating a parasitic infestation in an animal, which comprises administering a therapeutically effective amount of a compound or salt as defined in any one of claims 1 to 8, or administering a formulation thereof, as defined in claim 12.

* * * * *